(12) United States Patent
Dugar et al.

(10) Patent No.: US 11,492,339 B2
(45) Date of Patent: Nov. 8, 2022

(54) PROCESSES FOR CONVERSION OF BIOLOGICALLY DERIVED MEVALONIC ACID

(71) Applicant: Visolis, Inc., Berkeley, CA (US)

(72) Inventors: Deepak Dugar, Berkley, CA (US); Brian Neltner, Oakland, CA (US)

(73) Assignee: Visolis, Inc., Berkeley, CA (US)

( * ) Notice: Subject to any disclaimer, the term of this patent is extended or adjusted under 35 U.S.C. 154(b) by 123 days.

(21) Appl. No.: 17/024,770

(22) Filed: Sep. 18, 2020

(65) Prior Publication Data

US 2021/0078966 A1    Mar. 18, 2021

Related U.S. Application Data

(63) Continuation of application No. 16/278,570, filed on Feb. 18, 2019, now Pat. No. 10,807,963, which is a continuation of application No. 14/950,645, filed on Nov. 24, 2015, now Pat. No. 10,208,008.

(60) Provisional application No. 62/084,689, filed on Nov. 26, 2014.

(51) Int. Cl.
| | | |
|---|---|---|
| *C07C 1/207* | (2006.01) | |
| *C07D 309/30* | (2006.01) | |
| *C07C 45/66* | (2006.01) | |
| *C12P 7/42* | (2006.01) | |

(52) U.S. Cl.
CPC ............ *C07D 309/30* (2013.01); *C07C 1/207* (2013.01); *C07C 45/66* (2013.01); *C12P 7/42* (2013.01); *C07C 2521/04* (2013.01); *C07C 2521/06* (2013.01); *C07C 2521/08* (2013.01); *C07C 2521/10* (2013.01); *C07C 2521/12* (2013.01); *C07C 2523/44* (2013.01); *C07C 2529/40* (2013.01)

(58) Field of Classification Search
CPC ....... C07D 309/30; C07C 1/207; C07C 45/66; C07C 2521/04; C07C 2521/06; C07C 2521/08; C07C 2521/10; C07C 2521/12; C07C 2523/44; C07C 2529/40; C12P 7/42
See application file for complete search history.

(56) References Cited

U.S. PATENT DOCUMENTS

| | | |
|---|---|---|
| 4,423,271 A | 12/1983 | Obenaus et al. |
| 4,792,620 A | 12/1988 | Paulik |
| 4,866,140 A | 9/1989 | Gutierrez et al. |
| 5,049,693 A | 9/1991 | Himmler |
| 5,262,552 A | 11/1993 | Takano et al. |
| 8,404,890 B2 | 3/2013 | Dumesic et al. |
| 8,410,326 B2 | 4/2013 | Dumesic et al. |
| 8,513,151 B2 | 8/2013 | Lemcoff et al. |
| 8,513,467 B2 | 8/2013 | Dumesic et al. |

FOREIGN PATENT DOCUMENTS

| | | |
|---|---|---|
| WO | 2007/111783 A2 | 10/2007 |
| WO | 2007/111783 A3 | 10/2007 |
| WO | 2009/076676 | 6/2009 |
| WO | 2009076676 A2 | 6/2009 |
| WO | 2011/160081 A1 | 12/2011 |
| WO | 2011160081 A1 | 12/2011 |
| WO | 2014/152309 A1 | 9/2014 |
| WO | 2014/172596 A2 | 10/2014 |
| WO | 2016/077555 A1 | 5/2016 |
| WO | 2016077555 A1 | 5/2016 |

OTHER PUBLICATIONS

Xiong, Mingyong et al., Scalable production of mechanically tunable block polymers from sugar, University of Minnesota, PNAS, www.pnas.org/cgi/doi/10.1073/pnas.1404596111, vol. 111, No. 23, pp. 8357-8362, Jun. 10, 2014.
Zhao, R et al., NAD-dependent Lactate Dehydrogenase Catalyses the First Step in Respiratory Utilization of Lactate by Lactococcus Lactis, FEBS, Open Bio. 2013, vol. 3, pp. 379-386, p. 380, left col., 3rd paragraph; figure 5.
Search Report and Written Opinion dated Feb. 4, 2016 for related PCT Application No. PCT/US2015/062433, 15 pages.
Duggan, M.J. et al., Copper(I) Chloride Catalyzed Addition of Alcohols to Alkyl Isocyanates A mild and Expedient Method for Alkyl Carbamate Formation, Synthesis, vol. 2, 1989, pp. 131-132.
White, J.D. et al., Stereoselective synthesis of the macrocycle segment of verrucarin J, Journal of Organic Chemistry, vol. 47, No. 6, 1982, pp. 929-932.
White, J.D., et al., Synthesis of (+/−)-lineatin, an aggregation pheromone of Trypodendron lineatum, Journal of the American Chemical Society, vol. 104, No. 20, 1982, pp. 5486-5489.
Matsumi, R. et al., Biocatalytic asymmetric phosphorylation of mevalonate, RSC Advances, vol. 4, No. 25, Feb. 21, 2014, p. 12989-12994.
Orrling, K.M. et al., Fast, Acid-Free, and Selective Lactamization of Lactones in Ionic Liquids, Journal of Organic Chemistry, vol. 73, No. 21, Oct. 1, 2008, pp. 8627-8630.

(Continued)

*Primary Examiner* — Thuan D Dang
(74) *Attorney, Agent, or Firm* — Hovey Williams LLP; Kameron D. Kelly

(57) ABSTRACT

A process is provided for converting mevalonic acid into various useful products and derivatives. More particularly, the process comprises reacting mevalonic acid, or a solution comprising mevalonic acid, in the presence of a solid catalyst at an elevated temperature and pressure to thereby form various biobased products. The process may also comprise: (a) providing a microbial organism that expresses a biosynthetic mevalonic acid pathway; (b) growing the microbial organism in fermentation medium comprising suitable carbon substrates, whereby biobased mevalonic acid is produced; and (c) reacting the biobased mevalonic acid in the presence of a solid catalyst at an elevated temperature and pressure to yield various biobased products.

16 Claims, 1 Drawing Sheet
Specification includes a Sequence Listing.

(56) References Cited

OTHER PUBLICATIONS

Takano, S. et al., A facile conversion of natural (R)-Mevalonolactone into a vitamin E key intermediate, Heterocycles, vol. 31, No. 5, 1990, pp. 917-921.
Yamashita, H. et al., Commercial production of mevalonolactone by fermentation and the application to skin cosmetics with anti-aging effect, Fragrance Journal, vol. 28, No. 2, 2000, pp. 62-65.
European Search Report dated Jun. 18, 2018 for related European Patent Application No. 15863103.6, 12 pages.
Norskov et al.; Nature Chemistry, Towards the Computational Design of Solid Catalysts, 2009, 1, pp. 37-46.
EP Examination Report dated Feb. 4, 2020 for related European Patent Application No. 15863103.6; 7 pages.
JP Second Office Action dated Feb. 18, 2020 for related Japanese Patent Application No. 2017-526062; 8 pages.
Renee M. Thomas et al., Highly Selective Ruthenium Metathesis Catalysts for Ethenolysis, The Arnold and Mabel Beckman Laboratories of Chemical Synthesis, Pasadena, California, pp. 7490-7496, pubs.acs.org/JACS, received with Japanese 2nd Office Action.
Gasparic et al., Bioorganic Model of Isoprene Formation from Mevalonic Acid in Vitro, Folia Pharmaceutica Universitatis Carolinae, 2003, 27-28, pp. 35-41.
Okuhara, Water-Tolerant Solid Acid Catalysts, Chemical Reviews, 2002, 102, 3641-3666.

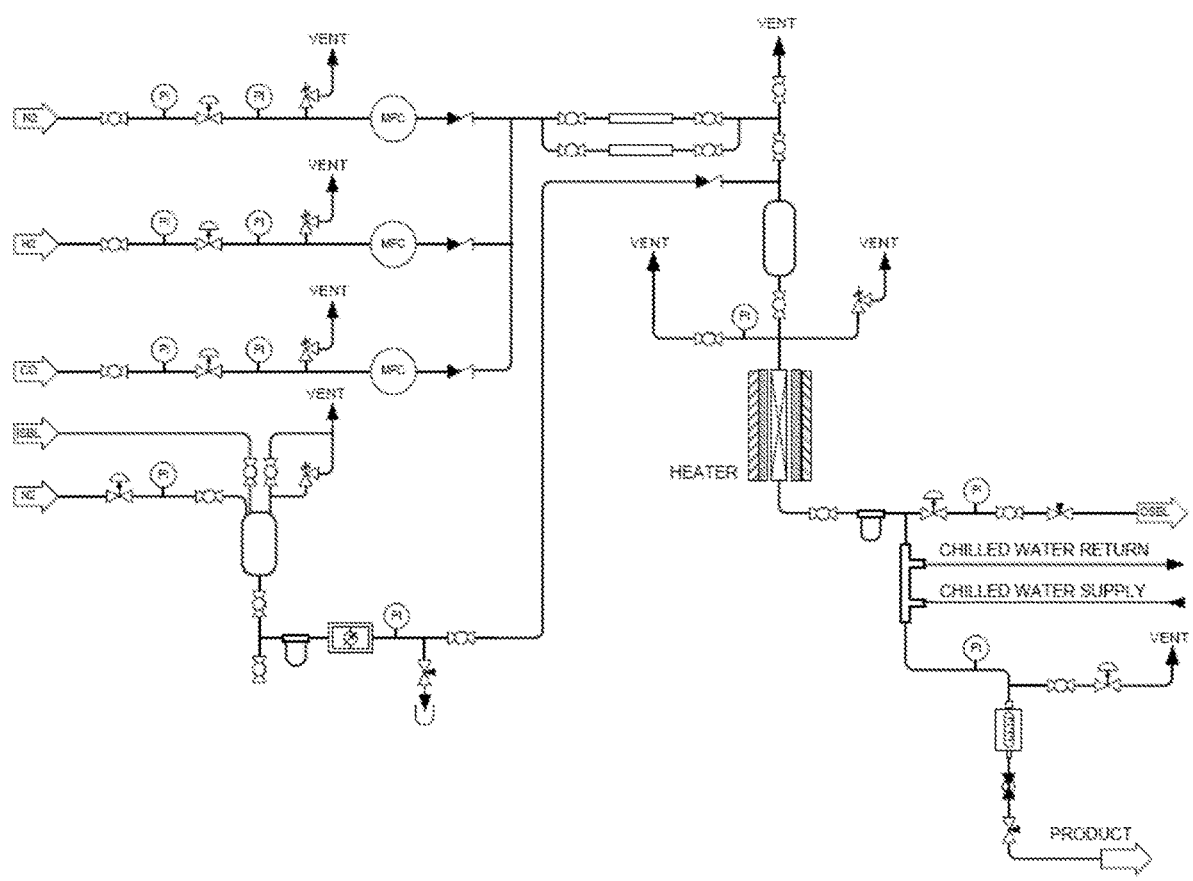

PROCESSES FOR CONVERSION OF BIOLOGICALLY DERIVED MEVALONIC ACID

CROSS-REFERENCE TO RELATED APPLICATIONS

The present application is a continuation of U.S. patent application Ser. No. 16/278,570, filed Feb. 18, 2019, entitled PROCESSES FOR CONVERSION OF BIOLOGICALLY DERIVED MEVALONIC ACID, which is a continuation of U.S. patent application Ser. No. 14/950,645, filed Nov. 24, 2015, entitled PROCESSES FOR CONVERSION OF BIOLOGICALLY DERIVED MEVALONIC ACID, which has issued as U.S. Pat. No. 10,208,008 and claims the priority benefit of U.S. Provisional Patent Application Ser. No. 62/084,689, filed Nov. 26, 2014, entitled PROCESSES FOR CONVERSION OF BIOLOGICALLY DERIVED MEVALONIC ACID, all of which are incorporated by reference in their entireties herein.

SEQUENCE LISTING

The following application contains a sequence listing in computer readable format (CRF), submitted as a text file in ASCII format entitled "46567SequenceListing," created on Nov. 23, 2015, as 25 KB. The content of the CRF is hereby incorporated by reference.

BACKGROUND OF INVENTION

Technical Field

The present invention relates generally to processes for producing intermediates for hydrocarbon biofuels and other products from organic acids that are derived from via biochemical routes. In particular, Mevalonic acid (or Mevalonolactone) can be derived from biomass fermentation to produce a variety of intermediates. One or more embodiments of the present invention relate to production of isoprene, methyl vinyl ketone, 3-methyl-2-butanone, and anhydro-mevalonolactone.

Description of Related Art

Organic acids are an important class of compounds that can be derived via biochemical routes and can serve as intermediates for the sustainable production of hydrocarbon biofuels and other products. Of particular interest is the dehydration/decarboxylation to form isoprene, a critical starting material for a variety of synthetic polymers (i.e., synthetic rubbers), specialty chemicals, and a gasoline additive, known as alkylate. While isoprene can be obtained by fractionating petroleum, the purification of this material is expensive and time-consuming. In addition, the depletion of fossil fuels makes it crucial that another source of this vital starting material be found. Isoprene is naturally produced by a variety of microbial, plant, and animal species. However, the yield of isoprene from naturally-occurring organisms is commercially unattractive. Thus, a large scale synthesis of isoprene, and other synthetically useful intermediates, from biomass-derived mevalonolactone would have substantial commercial potential.

SUMMARY OF THE INVENTION

In one aspect, the invention is concerned with a process comprising: (a) reacting MVL, or a solution comprising MVL, in the presence of a solid catalyst to yield a first product or first product mixture, wherein the solution comprising MVL optionally comprises anhydro-mevalonolactone and/or a co-reactant.

In some embodiments the co-reactant is selected from the group consisting of water, alkyl alcohol, ethers, aromatic compounds, acids, aldehydes, esters, and mixtures thereof. In some embodiments, step (a) occurs at a temperature in the range of about 100° C. to about 500° C. In some embodiments, step (a) occurs at a pressure in the range of about sub-atmospheric pressure to about 200 bar.

In some embodiments the solid catalyst is a solid acid catalyst. A non-limiting, illustrative list of potentially suitable solid catalysts includes functionalized styrene-divinyl-benzene copolymers, functionalized tetrafluoroethylene-fluoropolymer copolymers, calcium apatite, silica-alumina, silica, titania, alumina, resins, metal oxides, and/or zeolites.

In some embodiments the solid catalyst is selected from the group consisting of a metal oxide catalyst and a carbon catalyst. In some embodiments the solid catalyst has a surface area between about 20 $m^2/g$ and about 600 $m^2/g$. In some embodiments of the solid catalyst is selected from the group consisting of silicon oxide, aluminum oxide, titanium oxide, magnesium oxide, zirconium oxide, cobalt oxide, iron oxide, nickel oxide, manganese oxide, zinc oxide, molybdenum oxide, tungsten oxide, calcium oxide, cerium oxide, tin oxide, and chromium oxide, and mixtures thereof. In some embodiments the solid catalyst comprises a mixed metal oxide catalyst.

In some embodiments of the invention the solid catalyst comprises a supported transition or noble metal, e.g., palladium, magnesium, vanadium, chromium, manganese, iron, cobalt, nickel, copper, zinc, zirconium, molybdenum, ruthenium, rhodium, silver, tin, tungsten, tantalum, iridium, platinum, and gold, and mixtures thereof.

In some embodiments, the first product or first product mixture comprises one or more of isoprene, 3-methyl-2-butanone, methyl vinyl ketone, anhydro-mevalonolactone, 2-pentene, 2-methyl-1-butene, 2-methyl-1-pentene, methane, hydrogen, or an alkyl alcohol.

In some embodiments of the invention, the previously described process comprises an additional step of: (b) reacting said first product or first product mixture with a first reagent and a second catalyst to yield a second product or second product mixture, wherein said first reagent is water or an olefin or an alcohol. In some embodiments the first reagent is an olefin and said second catalyst is selected from the group consisting of palladium, platinum, ruthenium, molybdenum, tungsten, rhenium, tin, and rhodium olefin metathesis catalysts, and mixtures thereof. In some embodiments the first reagent is an alcohol and said second catalyst is selected from the group consisting of homogenous and heterogeneous acids and bases, sugars, lipases, ion exchange resins, metal oxides, and zeolites, and mixtures thereof.

In some embodiments, the previously described step (b) occurs at a temperature in the range of about 100° C. to about 500° C. In some embodiments this process further comprises a step of: (c) reacting said second product or second product mixture with a second reagent and a third catalyst to yield a third product or third product mixture.

In another aspect, the invention provides a process comprising: (a) reacting MVL, or a solution comprising MVL, at a temperature in the range of about 100° C. to about 500° C. to yield a first product or first product mixture.

And yet another aspect, the invention provides a process comprising: (a) providing a microbial organism that expresses a biosynthetic MVL pathway; (b) growing the microbial organism in fermentation medium comprising suitable carbon substrates, whereby biobased MVL is produced; and (c) reacting said biobased MVL to yield a first product or first product mixture. Step (c) optionally occurs in the presence of a solid catalyst and/or at a temperature in the range of about 100° C. to about 500° C.

In some embodiments, a microbial organism used in the above described process is a non-naturally occurring microbial organism comprising a metabolic modification that enables biobased MVL production.

In some embodiments, the metabolic modifications comprises expression of at least one gene set selected from the group consisting of: i. mvaE, mvaS; ii. mvaE, mvaS, atoB; iii. atoB, hmgR, hmgS; and iv. functional homologs of i, ii, or iii.

In some embodiments, the metabolic modification comprises modification of at least one gene, e.g., ackA-pta, adhE, and/or ldhA.

In some embodiments, the fermentation medium used comprises a renewable feedstock.

BRIEF DESCRIPTION OF THE DRAWINGS

FIG. 1 is a schematic diagram of a high pressure small scale unit used in Example 11.

DETAILED DESCRIPTION

Mevalonic acid, mevalonate, and mevalonolactone exist in an equilibrium which is pH dependent. Thus, a solution which contains "mevalonate" may actually contain mevalonic acid, mevalonate, and/or mevalonolactone. In addition, depending on the pH, the components may be in salt form. Depending on the reagent chosen, the counter ion can be the cation of ammonium, sodium, lithium, potassium, magnesium, calcium, aluminum, or cesium. For convenience, mevalonolactone or "MVL" will be used herein inclusively.

Mevalonolactone (MVL) and its related derivatives, such as 2,3-dehydromevalonolactone (4-methyl-5,6-dihydro-2H-pyran-2-one; also referred to as anhydromevalonolactone, AML) represent a potentially abundant feedstock that may be prepared on an industrial scale. Biobased production via fermentation allows for the high-yielding and cost competitive production of MVL from renewable feedstocks with low volatility, such as sugars, glycerin, syngas, or methane. Chemical products produced from biobased MVL and its related derivatives could fill a need for inexpensive, renewable consumer and industrial products not based on petroleum or other nonrenewable resources. Biobased mevalonolactone can subsequently be converted into a variety of useful compounds. Exemplary compounds are described herein, and also in co-pending U.S. Ser. No. 14/939,437, filed Nov. 12, 2015, incorporated by reference herein in its entirety.

The term "biobased" as used herein means that the compound was synthesized from a biological precursor, and specifically a renewable biological carbon source, such as biomass (as opposed to a non-renewable petroleum-based carbon source). ASTM has set a method standard to calculate the level of biobased material included in a composition: ASTM D6866—Standard Test Methods for Determining the Biobased Content of Solid, Liquid, and Gaseous Samples Using Radiocarbon Analysis. The biobased content of a composition is the amount of biobased carbon in the material as fraction weight (mass) or percent weight (mass) of the total organic carbon in the material. ASTM D6866 is similar to radiocarbon dating without the age equations. It is done by determining a ratio of the amount of radiocarbon (14C) in the material to that of a modern reference standard. The ratio is reported as a percentage referred to as percent modern carbon (units "pMC"). If the material being analyzed is a mixture of present day radiocarbon and fossil carbon (i.e., containing no radiocarbon), then the pMC value obtained correlates directly to the amount of biobased material present in the sample.

ASTM D6866 distinguishes carbon resulting from contemporary biomass-based input material from those derived from fossil-based material. Biomass contains a well-characterized amount of Carbon-14 that is easily differentiated from other materials such as fossil fuels that do not contain any Carbon-14. "Biomass" is generally defined as plant material, vegetation or agricultural waste used as a fuel or energy source. The ratio of carbon-14 isotope to carbon-12 isotope for biomass carbon is generally known to those skilled in the art to be about $2 \times 10^{-12}$ to 1 based on the current natural abundance of carbon-14 to carbon-12 as taken from air samples. Since the amount of Carbon-14 in biomass is known, a percentage of carbon from renewable sources can be calculated easily from the total organic carbon in the sample. Zero percent Carbon-14 indicates a complete lack of Carbon-14 atoms in a material, thus indicating a fossil or petroleum-based carbon source. Likewise, 100% Carbon-14 (after atmospheric correction) indicates a modern biobased carbon source.

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). This was a logical point in time to use as a reference for archaeologists and geologists. For reference, an archaeologist or geologist using radiocarbon dates, AD 1950 equals "zero years old." It also represents 100 pMC. "Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It has gradually decreased over time with today's value being near 105 pMC. This means that a fresh biomass material such as corn, sugar cane or soybeans would give a radiocarbon signature near 105 pMC. By presuming ~105 pMC represents present day biomass materials and 0 pMC represents petroleum derivatives, the measured pMC value for that material will reflect the proportions of the two component types. For example, a material derived 100% from present day soybeans would give a radiocarbon signature near 105 pMC. But if it was diluted with 50% petroleum carbon, it would give a radiocarbon signature near 53 pMC.

The "biobased content" of a material is reported as a percent value relating total renewable organic carbon to total organic carbon. The final result is calculated by multiplying the pMC value measured for the material by 0.95 (to adjust for bomb carbon effect). The final % value is cited as the mean biobased result and assumes all the components within the analyzed material were either present day living (within the last decade) or fossil in origin. In one aspect, the materials used in the invention (e.g., precursor compounds or resulting polymers) have a biobased content of greater than 0%, more preferably greater than 10%, more preferably greater than 25%, more preferably greater than 50%, and even more preferably greater than 75%. Preferably, the materials used in the invention are substantially entirely biobased according to ASTM D6866, which means they are 95 percent or more of biological origin. Thus, it will be appreciated that biobased products can be distinguished from petroleum-based products by carbon finger-printing. Thus, biobased polymers and polymeric precursors according to the invention will have a higher radioactive Carbon-14 (14C) content or a higher 14C/12C ratio than the same type of polymer of petroleum (non-renewable) origin. In one aspect, the biobased polymeric precursors and/or resulting polymers will have a 14C/12C ratio of greater than 0, preferably greater than 1.

The biobased MVL can serve as a common starting material for the production of several classes of polymers, as described in co-pending U.S. Ser. No. 14/939,437.

For example, MVL and AML themselves are monomers for polymerization reactions. The lactone structure of MVL and AML allows for ring-opening co-polymerization. The ring-opening co-polymerization of MVL-derived β-methyl-δ-valerolactone has been reported previously. In addition to ring-opening polymerization, AML may be a co-monomer for free radical polymerization reactions. During the dehydration reaction of MVL different AML isomers, differing by the position of the unsaturation, i.e., 3,4-dehydromevalonolactone (4-methyl-3,6-dihydro-2H-pyran-2-one), 4,5-dehydromevalonolactone (4-methyl-3,4-dihydro-2H-pyran-2-one), and exo-dehydromevalonolactone (4-methylenetetrahydro-2H-pyran-2-one), can be obtained. These isomers may be utilized as monomers for ring-opening and free radical polymerization similar to AML.

In addition to the direct polymerization of MVL and related compounds described above, they can be converted into building blocks for step-growth polymers, such as diols and diacids among others. These conversions can be broadly categorized by the type of chemical reaction: i) Oxidation, ii) Reduction, iii) Lactone ring-opening, iv) Olefin modification, and v) Alcohol modification.

Full oxidation of MVL and related lactones to afford alpha,omega-dicarboxylic acids can be realized by treatment with high-valent metal oxides such as $CrO_6$, or $KMnO_4$ among others, which can also be employed in catalytic amounts in the presence of a stoichiometric strong oxidant. The oxidation of primary alcohols to carboxylic acids is also possible with nitric acid, or molecular oxygen as the oxidant. Examples of above reagents can be found for carboxylic acid as well as lactone oxidation. The MVL-derived dicarboxylic acids may find use as building blocks for polyesters, alkyd resins, unsaturated polyester resins, polyester polyols, or polyamides to name a few.

Full reduction of MVL and related lactones leads to substituted alpha,omega-diols. Metal hydrides, such as lithium tetrahydridoaluminate, elemental sodium or hydrogen in the presence of a metal catalyst can be employed to reduce the lactone functional group to two primary alcohols. These MVL-derived di-, and polyols may be used as building blocks for polyesters, alkyd resins, unsaturated polyester resins, polyester polyols, polycarbonates, or vinyl-urethane resins among others.

Nucleophiles such as alcohols, thiols, or amines are able to ring-open lactones. The reaction of MVL and related lactones with di-, or multifunctional nucleophiles results in the formation of substituted ring-opened MVL-based di-, or polyols. The nucleophiles can be either homofunctional, e.g. glycerol, or ethylene diamine among others, or heterofunctional, such as ethanolamine, or mercapto ethanol among others. The uses of these ring-opened derivatives are equivalent to the above mentioned MVL reduction products.

Modifications of the alkene group in AML and its isomers include epoxidation, dihydroxylation, Michael addition, Diels-Alder reaction, or [2+2]-cycloaddition among others. The reaction products are diverse in functionality, and possibly serve as building blocks for a variety of polymers. The lactone functionality is preserved in all the above mentioned reactions. Ring-opening polymerization of these compounds can result in the formation of modified aliphatic polyester with applications as thermoplastic elastomers, unsaturated polyester resins, or polyurethanes among others.

The tertiary alcohol in MVL can be modified to form ether and ester derivatives. Functional groups promoting polymerization, or properties such as solubility and adhesion can be introduced. It has been reported that a methacrylate with pendant MVL ester group can be obtained from MVL. It can be envisioned that this bi-functional adduct is able to participate in free-radical and ring-opening polymerization to produce acrylics and vinyl polyesters.

The MVL-derived di-, or polyols and -acids can also serve as precursors for epoxy resins, poly(vinylether)s, or multifunctional cyclic carbonates.

In some embodiments, the invention provides a process that comprises a first step of reacting MVL, or a solution comprising MVL, under conditions that yield a first product or first product mixture. In an optional second step, the first product or first product mixture can then be further reacted with a reagent, optionally in the presence of a catalyst. In some embodiments of the invention, the reagent is an olefin or an alcohol. In an optional third step, the second product or second product mixture resulting from this reaction can be reacted with the same or another reagent, again optionally in the presence of a catalyst to produce a third product or third product mixture. As used herein, the term "product mixture" refers to a mixture of structurally distinct compounds.

In certain aspects of the invention, a product or product mixture comprises polymer precursor compounds (aka polymer building blocks) of biobased MVL or MVL derivatives, such as described in co-pending U.S. Ser. No. 14/939,437. In one or more embodiments, a polymer precursor compound of the invention comprises ring-opened biobased MVL or derivatives thereof. Examples of polymer precursor compounds of the invention include biobased MVL-diols, biobased MVL-diacids, and biobased MVL-glycidyl ether/esters. The invention facilitates the synthesis of compositions comprising one or more of the ring-opened biobased MVL compounds, including polymers prepared from one or more of the foregoing biobased MVL precursor compounds. The invention further provides a variety of other biobased polymers and oligomers prepared from biobased MVL or derivatives as described herein.

In more detail, described herein are compounds (e.g., monomers, oligomers, and/or polymers) derived from biobased compounds, and specifically biobased MVL and its related derivatives, and processes for synthesizing these compounds. Through oxidation, for example, these biobased precursors can be reacted to yield building blocks for (unsaturated-) polyesters, polyester polyols and polyamides, as well as precursors for glycidyl esters and omega-alkenyl esters (e.g., allyl ethers, homoallyl ethers, vinyl ethers, etc.).

The process steps of the invention are preferably carried out in solution, e.g., in the presence of a solvent. In some embodiments the solvent functions as a co-reactant by reacting with MVL, a derivative of MVL, or some other compound derived from MVL. In some embodiments of the invention, water is used as the solvent. Other solvents, such as linear, branched, or cyclic alcohols or diols (i.e., methanol, ethanol, propanol, isopropanol, sec-butanol, cyclobutanol, glycerol, 2-ethyl hexanol, propanediol, butanediol, lauryl alcohol, etc.) may also be used. Other suitable solvents include polar, aprotic solvents such as tetrahydrofuran (THF), other linear or cyclic ethers, dimethyl sulfoxide (DMSO), dimethylformamide (DMF), dioxane, etc. as a general matter, alkyl alcohol, ethers, aromatic compounds, acids, aldehydes, esters all can function as effective solvents and co-reactants in various embodiments of the invention, as will be readily discernible to one of skill in the art. Mixtures of water and these solvents (and other suitable solvents) may also be used.

In some embodiments of the invention, one or more of the process steps occurs in the presence of a catalyst. The catalyst can be a currently known catalyst, or a catalyst developed in the future. In some embodiments, the preferred catalyst, particularly, but not exclusively, with regard to the first step is a solid catalyst. Preferred catalysts of the invention include solid acid catalysts, metal oxide catalysts and carbon catalysts. A solid acid catalyst may comprise one or more solid acid materials without limitation, whether now known or developed in the future. Exemplary solid acid catalysts which can be utilized include, but are not limited to, heteropoly acids, acid resin-type catalysts, meso-porous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.), which may optionally be doped with additional acid groups such as sulfates, phosphates, etc., may also be used as solid acid catalysts. Further examples of suitable solid acid catalysts include strongly acidic ion exchangers such as cross-linked polystyrene containing sulfonic acid groups. For example, the Amberlyst Resins® are functionalized styrene-divinylbenzene copolymers with different surface properties and porosities. The functional group is generally that of the sulfuric acid type. The Amberlyst Resins® are supplied as gellular or macro-reticular spherical beads (Amberlyst® is a registered trademark of the Dow Chemical Co., Midland, Mich.). Similarly, Nafion Resins® are sulfonated tetrafluoroethylene-based fluoropolymer copolymers which are solid acid catalysts (Nafion® is a registered trademark of E.I. du Pont de Nemours & Co., Wilmington, Del.). Zeolites may also be used as solid acid catalysts. Of these, H-type zeolites are generally preferred, for example zeolites in the mordenite group or fine-pored zeolites, such as zeolites X, Y, and L (i.e., mordenite, erionite, chabazite, or faujasite). Additional zeolites are the ultrastable zeolites in the faujasite group which have been dealuminated. The solid acid catalyst is preferably selected from the group consisting of functionalized styrene-divinylbenzene copolymers, functionalized tetrafluoroethylene-fluoropolymer copolymers, calcium apatite, silica-alumina, silica, titania, alumina, resins, metal oxides, and zeolites.

In some preferred embodiments of the invention, the catalysts used is selected from the group consisting of silicon oxide, aluminum oxide, titanium oxide, magnesium oxide, zirconium oxide, cobalt oxide, iron oxide, nickel oxide, manganese oxide, zinc oxide, molybdenum oxide, tungsten oxide, calcium oxide, cerium oxide, tin oxide, and chromium oxide, and mixtures thereof. Some preferred embodiments of the invention employ a solid catalysts that comprises a mixed metal oxide catalyst, i.e., a catalyst comprising two or more distinct metals or metal oxides. In some preferred embodiments, a process of the invention employs a heterogeneous catalyst. In some embodiments, potassium bisulfate is excluded from the list of solid acid catalysts, for the first catalyst.

In some embodiments, a solid catalyst used in the invention comprises a supported transition or noble metal. An illustrative, non-limiting list of transition or noble metals encompassed by the invention includes palladium, magnesium, vanadium, chromium, manganese, iron, cobalt, nickel, copper, zinc, zirconium, molybdenum, ruthenium, rhodium, silver, tin, tungsten, tantalum, iridium, platinum, and gold, and mixtures thereof.

In some embodiments of the invention, where the second step involves reaction with an olefin, a catalyst is employed that is selected from the group consisting of ruthenium, molybdenum, tungsten, rhenium, tin, and rhodium olefin metathesis catalysts, and mixtures thereof. In other embodiments, where the second step involves reaction with an alcohol, a catalyst is employed that is selected from the group consisting of homogenous and heterogeneous acids and bases, sugars, lipases, ion exchange resins, metal oxides, and zeolites, and mixtures thereof.

Catalyst of the invention are characterized by a wide range of surface areas. In some embodiments, a solid catalyst is used having a surface area equal to or greater than 1 $m^2/g$, 5 $m^2/g$, 10 $m^2/g$, 20 $m^2/g$, 50 $m^2/g$, 100 $m^2/g$, or 200 $m^2/g$. In some embodiments, a solid catalyst is used that has a surface area equal to or less than 50 $m^2/g$, 100 $m^2/g$, 200 $m^2/g$, 600 $m^2/g$, 1000 $m^2/g$, or 2000 $m^2/g$. As one illustrative but non-limiting example, in some preferred embodiments the solid catalyst has a surface area between 20 $m^2/g$ and 600 $m^2/g$.

In some embodiments, the first product or first product mixture comprises one or more of isoprene, 3-methyl-2-butanone, methyl vinyl ketone, anhydro-mevalonolactone, 2-pentene, 2-methyl-1-butene, 2-methyl-1-pentene, methane, hydrogen, or an alkyl alcohol.

In some embodiments, the first product or first product mixture comprises compounds independently selected from the group consisting of

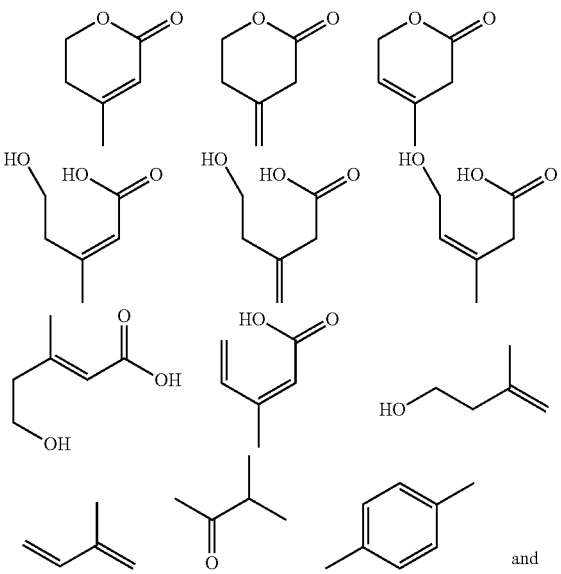

and

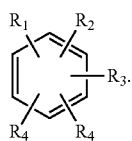

wherein $R_1$, $R_2$, $R_3$, $R_4$, and $R_5$ are independently selected from the group consisting of H, branched and unbranched $C_1$-$C_3$ alkyl and branched and unbranched $C_2$-$C_4$ alkenyl.

In a preferred embodiment, the first product or first product mixture comprises compounds independently selected from the group consisting of

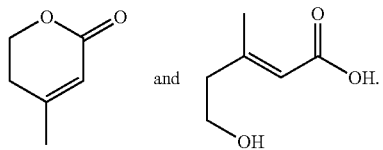

In one embodiment, the olefin of the optional second step is preferably selected from the group consisting of branched and unbranched $C_2$-$C_{20}$ alkenes, branched and unbranched $C_3$-$C_{20}$ alkenic acids, branched and unbranched $C_3$-$C_{20}$ alkenoic acid esters, wherein the olefin is optionally substituted. The olefin is more preferably selected from the group consisting of ethene, propene, 1-butene, 2-butene, 2-methyl-2-propene, acrylic acid, palmitoleic acid, oleic acid, linoleic acid, and arachidonic acid, and esters thereof.

The second step may further comprise a second catalyst. In one embodiment the second catalyst is preferably an olefin metathesis catalyst selected from the group consisting of palladium, platinum, ruthenium, molybdenum, tungsten, rhenium, tin, and rhodium olefin metathesis catalysts, and mixtures thereof. Examples of specific catalysts can be found in the primary literature, the patent literature, and reviews, such as Grubbs, R. H. et al. *J. Am. Chem. Soc.* 2011, 133, 7490-7496; Kadyrov, R. et al. *Top. Catal.* 2012, 55, 538-542; Hoveyda, A. H. et al. *J. Am. Chem. Soc.* 2009, 131(31), 10840-10841; Grubbs, R. H. et al. *J. Am. Chem. Soc.* 2012, 134(1), 693-699; Schrodi, Y. et al. *Clean* 2008, 36(9), 669-673; Elevance Renewable Sciences Inc. U.S. Patent Application Publication No. 2013/0289327; and Burk, M. J. et al. U.S. Patent Application Publication No. 2009/0155866. Preferred catalysts are shown below (Grubbs, R. H. et al. *J. Am. Chem. Soc.* 2011, 133, 7490-7496).

12

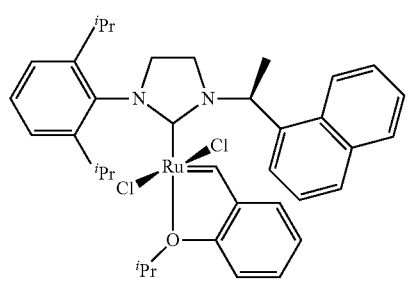

13

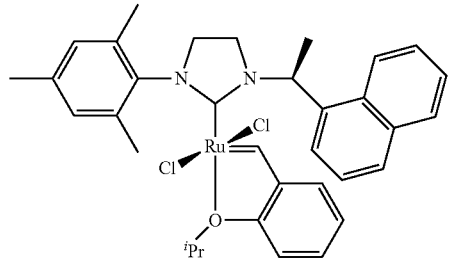

14

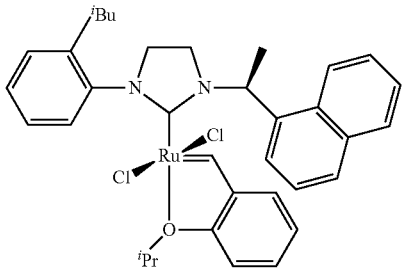

15

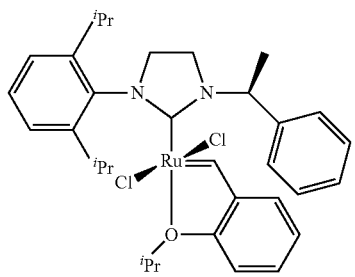

16

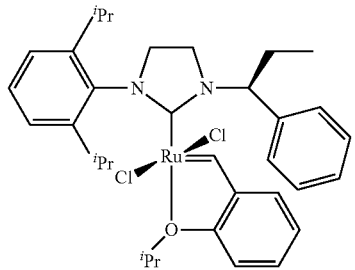

17

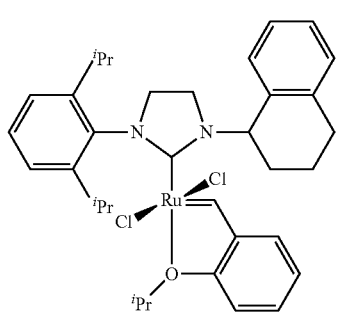

-continued

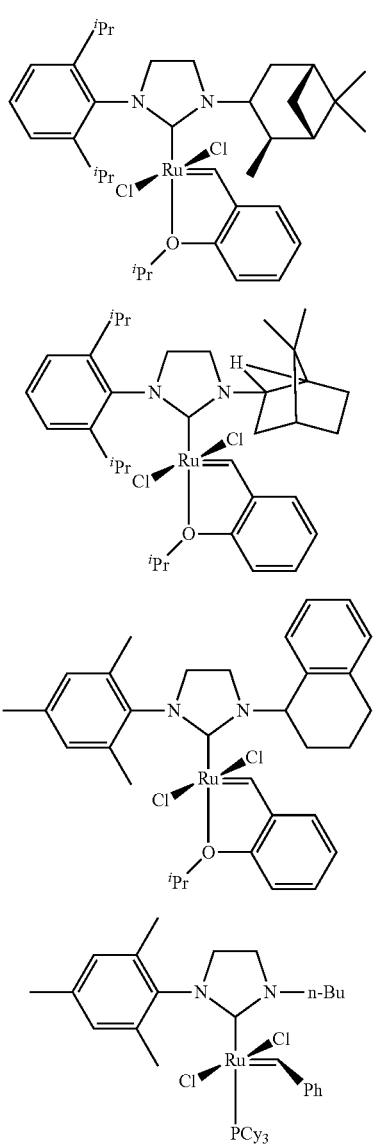

In one embodiment, the alcohol of the second step is preferably selected from the group consisting of branched and unbranched $C_1$-$C_{34}$ alkyl alcohols, branched and unbranched $C_2$-$C_{20}$ alkyl diols, and branched and unbranched $C_2$-$C_{34}$ alkenols. The alcohol is more preferably selected from the group consisting of methanol, ethanol, glycerol, 2-ethyl hexanol, propanediol, butanediol, and lauryl alcohol.

The second step may further comprise a second catalyst. In one embodiment, the second catalyst is preferably selected from the group consisting of homogenous and heterogeneous acids and bases, sugars, lipases, ion exchange resins, metal oxides, and zeolites. The second catalyst is more preferably selected from the group consisting of KOH, $KOCH_3$, $NaOCH_3$, NaOH, $H_2SO_4$, and mixtures thereof.

The International Union of Pure and Applied Chemistry (IUPAC) names for some of the chemical compounds described herein are as follows: Mevalonic acid: 3,5-dihydroxy-3-methylpentanoic acid; Mevalonolactone: 4-hydroxy-4-methyltetrahydro-2H-pyran-2-one; Dehydrated Mevalonolactone: 4-methyl-5,6-dihydro-2H-pyran-2-one (isomer one) and 4-methyl-3,6-dihydro-2H-pyran-2-one (isomer two); Dehydrated Mevalonic acid: (E)-5-hydroxy-3-methylpent-2-enoic acid (isomer one) and (E)-5-hydroxy-3-methylpent-3-enoic acid (isomer two).

It is preferred that after the first reaction, and before the second reaction, at least a fraction of any water present in the solution containing the compound or mixture of compounds is removed. The water separation step is optional, particularly if a water-tolerant catalyst is used in the second step, or water-dilution is not undesirable.

Reactions of the invention are preferably conducted in a range from about 250K to about 1000K. In some embodiments of the invention, a reaction step is performed at a temperature equal to or greater than about 25° C., 50° C., 100° C., 150° C., 200° C., 300° C., 400° C., or 500° C. In some embodiments of the invention, a reaction step is performed at a temperature less than or equal to about 100° C., 150° C., 200° C., 300° C., 400° C., 500° C., 600° C., or 750° C. Non-limiting but illustrative examples of temperature ranges employed in certain preferred embodiments of the invention include about 100° C. to 500° C., about 150° C. to 500° C., about 200° C. to 500° C., about 250° C. to 500° C., about 100° C. to 400° C., about 150° C. to 400° C., about 200° C. to 400° C., and about 250° C. to 500° C. Reactions of the invention can be performed either in the presence or absence of a catalyst, and is a general matter lower temperatures can be employed to good effect in the presence of the appropriate catalysts, which can be readily determined by one of skill in the art.

Reactions of the invention can also be performed at a range of pressures varying from between sub-atmospheric to extremely high. In some embodiments of the invention, a reaction step is performed at a pressure greater than equal to about atmospheric pressure, 2 bar, 5 bar, 10 bar, 20 bar, 35 bar, 50 bar, 100 bar, 200 bar, 500 bar, or even higher. In some embodiments of the invention, a reaction step is performed at a pressure less than or equal to atmospheric pressure, 2 bar, 5 bar, 10 bar, 20 bar, 35 bar, 50 bar, 100 bar, 200 bar, 500 bar, or 1000 bar. Non-limiting but illustrative examples of pressure ranges employed in certain preferred embodiments of the invention include 0 to 15 bar, 2 bar to 100 bar, 5 bar to 100 bar, 10 bar to 100 bar, 20 bar to 100 bar, 35 bar to 100 bar, and 50 bar to 100 bar. In some instances the desired output of the invention can be enhanced by means of using a combination of relatively high temperature and pressure, in the presence or absence of a catalyst. For example, in some embodiments of the invention one or more of the reactions occur at a temperature in the range of 100° C. to 500° C. and a pressure in the range of 20 bar to 100 bar, or at a temperature in the range of 200° C. to 500° C. and a pressure in the range of 20 bar to 100 bar.

In one embodiment, the product or product mixture yielded from the second step are independently selected from the group consisting of

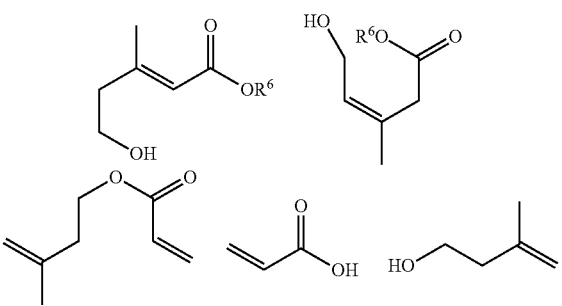

wherein R₆ is independently selected from the group consisting of branched and unbranched C₁-C₃₄ alkanes, branched and unbranched C₂-C₂₀ alkyl alcohols, and branched and unbranched C₂-C₃₄ alkenes, and more preferably selected from the group consisting of methyl, ethyl, glyceryl, 2-ethyl hexyl, 2-propanolyl, butanolyl, and lauryl.

In another embodiment, a product or product mixture of the second step may be combined at a third temperature and a third pressure with a reagent and a catalyst. In a preferred embodiment, the reagent is an olefin and the catalyst is preferably an olefin metathesis catalyst selected from the group consisting of palladium, platinum, ruthenium, molybdenum, tungsten, rhenium, tin, and rhodium olefin metathesis catalysts, and mixtures thereof. Examples of specific catalysts can be found in the primary literature, the patent literature, and reviews, such as Grubbs, R. H. et al. *J. Am. Chem. Soc.* 2011, 133, 7490-7496; Kadyrov, R. et al. *Top. Catal.* 2012, 55, 538-542; Hoveyda, A. H. et al. *J. Am. Chem. Soc.* 2009, 131(31), 10840-10841; Grubbs, R. H. et al. *J. Am. Chem. Soc.* 2012, 134(1), 693-699; Schrodi, Y. et al. *Clean* 2008, 36(9), 669-673; Elevance Renewable Sciences Inc. U.S. Patent Application Publication No. 2013/0289327; and Burk, M. J. et al. U.S. Patent Application Publication No. 2009/0155866. Preferred catalysts are shown in Scheme 1 (Grubbs, R. H. et al. *J. Am. Chem. Soc.* 2011, 133, 7490-7496). The olefin of the third step is preferably selected from the group consisting of branched and unbranched C₂-C₂₀ alkenes, branched and unbranched C₃-C₂₀ alkenic acids, branched and unbranched C₃-C₂₀ alkenoic acid esters, wherein the olefin is optionally substituted. The olefin is more preferably selected from the group consisting of ethene, propene, 1-butene, 2-butene, 2-methyl-2-propene, acrylic acid, palmitoleic acid, oleic acid, linoleic acid, and arachidonic acid, and esters thereof.

In another preferred embodiment, the reagent is an alcohol, and the catalyst is preferably selected from the group consisting of homogenous and heterogeneous acids and bases, sugars, lipases, ion exchange resins, metal oxides, and zeolites. The catalyst is more preferably selected from the group consisting of KOH, KOCH₃, NaOCH₃, NaOH, H₂SO₄, HCl, Amberlite Resin®, Amberlyst Resin®, CaO—CeO₂, ZSM-5 zeolites, and mixtures thereof. The alcohol of the third step is preferably selected from the group consisting of branched and unbranched C₁-C₃₄ alkyl alcohols, branched and unbranched C₂-C₂₀ alkyl diols, and/or branched and unbranched C₂-C₃₄ alkenols. The alcohol is more preferably selected from the group consisting of methanol, ethanol, glycerol, 2-ethyl hexanol, propanediol, butanediol, and/or lauryl alcohol.

In another embodiment, the product or product mixture resulting from the first step comprises molecules having C₈ or less. Depending on the pH, the components may be in salt form. In some embodiments, depending on the reagent chosen, the counter ion is independently selected from the cations of ammonium, sodium, lithium, potassium, magnesium, calcium, aluminum, and/or cesium.

In some embodiments the product or product mixture comprises a compound independently selected from the group consisting of

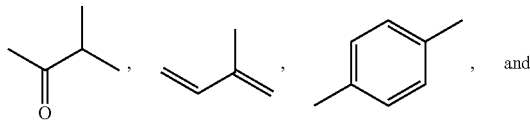
, and

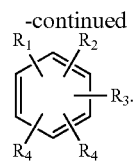

wherein R₁, R₂, R₃, R₄, and R₅ are independently selected from the group consisting of H, branched and unbranched C₁-C₃ alkyls, and branched and unbranched C₂-C₄ alkenyls.

One useful method for bio-production of a chemical product, such as biobased MVL, is fermentation. Fermentation procedures are well known to those of ordinary skill in the art. Fermentation of a set of complementary metabolizing organisms for the biosynthetic production of a target chemical compound, such as mevalonate, can be utilized in, for example, batch fermentation, fed-batch fermentation, or continuous fermentation. In addition, any of these methods of fermentation also can be coupled with well-known separation methods applicable to fermentation procedures such as batch separation or continuous separation. Exemplary combinations of fermentation and separation methods applicable for the bio-production of a target chemical compound such as mevalonate include, for example, batch fermentation and batch separation, batch fermentation and continuous separation, fed-batch fermentation and batch separation, fed-batch fermentation and continuous separation, continuous fermentation and batch separation, or continuous fermentation and continuous separation. Examples of batch and continuous fermentation procedures are well known in the art.

Mevalonate can be produced from both naturally and non-naturally occurring microbes. In some embodiments, the invention provides engineered, non-naturally occurring microbes capable of expressing MVL and/or MVL derivatives by means of a biosynthetic MVL pathway. The invention further provides processes of using both naturally and non-naturally occurring microbes capable of expressing, and preferably actually expressing, a biosynthetic MVL pathway in the production of biobased MVL and MVL derivatives. For example, in some embodiments the invention provides a process that comprise steps of (a) providing a microbial organism that expresses a biosynthetic MVL pathway; and (b) growing the microbial organism in fermentation medium comprising suitable carbon substrates, whereby biobased MVL is produced.

In some preferred embodiments, of the invention, invention provides a process that comprise steps of (a) providing a microbial organism that expresses a biosynthetic MVL pathway; (b) growing the microbial organism in fermentation medium comprising suitable carbon substrates, whereby biobased MVL is produced; and (c) reacting said biobased MVL to yield a product or product mixture. In some embodiments, the reaction occurs in the presence of a catalyst, preferably a solid catalyst. In some embodiments, the reaction occurs at elevated temperature and/or pressure. In some embodiments, this first product or product mixture is subsequently reacted further in one or more subsequent reactions. For example, the first product or product mixture can be reacted with an alcohol or olefin, optionally in the presence of a catalyst, and optionally at elevated temperature and/or pressure, as described above.

In some embodiments the invention provides methods for creating non-naturally occurring microbial organism by introducing a metabolic modification, for example a metabolic modification that enables biobased MVL production.

In some preferred embodiments, the metabolic modification includes at least one of the following gene sets: i. mvaE, mvaS; ii. mvaE, mvaS, atoB; and/or iii. atoB, hmgR, hmgS, or a functional homolog (or ortholog) thereof. The phrase "functional homolog" refers to a polynucleotide or polypeptide sequences that are similar due to common ancestry and sequence conservation and have identical or similar function at the catalytic, cellular, or organismal levels. Such a metabolic modification can enable stable production of mevalonate. The invention further provides the resulting non-naturally occurring microbial organisms, and methods of using the same in various processes embodying varying aspects of the invention. The mevalonate produced in any of the above-discussed processes may be used in integrated processes, such that the mevalonate is not isolated prior to the next step, or separated prior to the next step, as discussed above.

In some embodiments, the metabolic modifications further comprise modification or disruption of at least one gene. In a preferred embodiment, the gene is independently selected from the group consisting of adh1-adh7, gpd1, gpd2, ackA-pta, adhE and ldhA. In one embodiment, the non-naturally occurring microbial organism is selected from the group consisting of bacterium, yeast, algae, and fungus. Exemplary bacterium include species selected from the group consisting of *E. coli, A. succiniciproducens, A. succinogenes, M. succiniciproducens, R. etli, Bacillus subtilis, Corynebacterium glutamicum, Gluconobacter oxydans Zymomonas mobilis, Lactococcus lactis, Lactobacillus plantarum, Streptomyces coelicolor, Clostridium acetobutylicum, Clostridium sp., Synechococcus elongates, Pseudomonas fluorescens, Methanosarcina sp., Methylococcus sp.* and *Pseudomonas putida.* Exemplary yeast include species selected from the group consisting of *Saccharomyces cerevisiae, Schizosaccharomyces pombe, Kluyveromyces lactis, Kluyveromyces marxianus, Aspergillus terreus, Aspergillus niger, Rhizopus oryzae, Rhizopus arrhizus,* and *Pichia* sp. In some embodiments the microbial organism is a methanotrophic or photosynthetic microorganism, such as a methanotrophic or photosynthetic bacteria.

In one embodiment mevalonate can be produced utilizing naturally occurring *Saccharomycopsis fibuligera* IFO 0107 (Koike et al. *J. Ferm. Bioeng.* 1989, 68(1), 58-59). In another embodiment, mevalonate (MVA) was produced in a recombinant *E. coli* expressing genes for MVA biosynthesis. HMG-CoA synthase (mvaS) and bi-functional HMG-CoA reductase/acetyl CoaA acetyltransferase (mvaE) and acetyl CoaA acetyltransferase (atoB) were cloned to provide a route for the production of mevalonate in *E. coli* utilizing the endogenous acetyl-CoA pool. A similar process is demonstrated in the literature (Zhang, K. et al. *PNAS* 2014, 111(23), 8357-8362; Hashimoto, S.-I. et al. *Biotech. Let.* 2004, 26, 1487-1491; Endo, A. et al. *J. Ferm. Bioengin.* 1989, 68(1), 58-59).

In another embodiment, *E. coli* strain BL21(DE3), overexpressing codon optimized *E. feacalis* mvaE and mvaS genes driven by the T7 promoter, is cloned to provide a route for the production of mevalonate.

In another embodiment, *E. coli* strain *S. cerevisiae* CEN.PK, overexpressing codon optimized *E. feacalis* mvaE and mvaS genes, was cloned to provide a route for the production of mevalonate.

In another embodiment, *E. coli* strain BL21(DE3), overexpressing codon optimized *S. cerevisiae* hmgS and hmgR genes along with *E. coli* atoB gene, all driven by the T7 promoter, was engineered to provide a route for the production of mevalonate.

In another embodiment, mevalonate can be produced using *Clostridium* sp. MT1243 utilizing synthesis gas or a $CO_2/H_2$ blend as demonstrated in the literature (Kiriukhin, M. et al., *Bioprocess Biosyst. Eng.* 2014, 37, 245-260). Synthesis gas or syngas is available from a variety of carbonaceous materials, such as coal, acid-hydrolyzed lignocellulosic biomass, recovery of gas from steel mill emissions, or natural gas.

In another embodiment, *Chlorella protothecoides*, overexpressing codon optimized *E. faecalis* mvaS and mvaE genes along with *E. coli* atoB gene, all driven by the CaMV35S promoter, is engineered to provide a route for the production of mevalonate from $CO_2$ either under photoautotrophic, mixotrophic, or heterotrophic conditions.

In another embodiment, *Methylococcus capsulatus*, overexpressing codon optimized *E. faecalis* mvaS and mvaE genes along with *E. coli* atoB gene, all driven by the Trc promoter, is engineered to provide a route for the production of mevalonate from methane or methanol.

Fermentation of microbial organisms to produce mevalonate requires a source of carbon and energy, such as glucose, sucrose, xylose, arabinose, galactose, mannose, fructose, CO, $H_2$, or $CO_2$, and light or a combination of aforementioned. Exemplary materials and/or substrates supplying these energy sources include biomass, renewable feedstocks, natural gas, biogas, coal, and crude oil. Biomass is defined as any plant-derived organic material. Optimally, biomass for energy is obtained from a sustainable basis, such as herbaceous and woody energy crops, agricultural food and feed crops, agricultural crop wastes and residues, wood wastes and residues, aquatic plants, and other waste products (i.e., some municipal wastes). Sources of biomass that can be used as feedstocks are cellulosic biomass, hemicellulosic biomass, or lignocellulosic biomass, such as agricultural residue (i.e., wheat strass, corn stover, bagasse, wheat or cotton woodchips), reed canary grass, corn, wheat, cotton, wood chips, or energy crops (i.e., miscanthus). A renewable feedstock is defined as a renewable energy source, such as material derived from living organisms or their metabolic byproducts, including material derived from biomass. In addition to utilizing agricultural residue, crops grown for use as renewable feedstock include corn, soybeans, switchgrass, wheat, flaxseed, sugarcane, palm oil, and trees (i.e., poplar).

Biomass and renewable feedstocks are particularly useful sources of a variety of carbohydrates. In particular, glucose is available from a corn dry-grind process as demonstrated in the literature (Kwiakowski, J. R. et al. *Ind. Crops Prod.* 2006, 23, 288-296). For an example of the corn stover conversion to glucose, see Dudgeon, D. et al., *Process Design and Economics for Biochemical Conversion of Lignocellulosic Biomass to Ethanol: Dilute-Acid Pretreatment and Enzymatic Hydrolysis of Corn Stover* (National Renewable Energy Laboratory (NREL), Golden, Colo., 2011).

Previously-discussed biomasses and renewable feedstocks are useful sources for a variety of carbohydrates that can be used in a growth medium for complementary metabolizing organisms for the biosynthetic production. Particularly useful carbon sources include medium or feedstocks containing different simple or complex carbohydrates, useful for cellular proliferation. In one embodiment, nutrients and media comprise at least one carbon substrate selected the group consisting glucose, sucrose, xylose, arabinose, galactose, mannose, fructose, CO, and $CO_2$. In a preferred embodiment, the nutrients and media are a renewable feedstock. In one embodiment, the renewable feedstock is derived from biomass. In a preferred embodiment, the renewable feedstock is selected from the group consisting of a cellulosic biomass or a hemicellulosic biomass. In another embodiment, the renewable feedstock comprises a carbon source selected from the group consisting of carbohydrates, aromatic compounds, and lignin.

Additional advantages of the various embodiments of the invention will be apparent to those skilled in the art upon review of the disclosure herein and the working and/or prophetic examples provided below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds). Furthermore, whenever a number is provided that constitutes an upper or lower limit, or a numerical range, such as "equal or greater than 100," "less than or equal to 100," or "between 10 and 100," it should be understood that such limit or numerical range is to be construed as providing literal support for claim limitations that incorporate the word "about" prior to a numerical term. For example, "between 10 and 100" should be understood to provide literal support for a claim limitation reciting "between about 10 and between about 100."

EXAMPLES

The following examples set forth preferred methods in accordance with the invention. It is to be understood, however, that these examples are provided by way of illustration and nothing therein should be taken as a limitation upon the overall scope of the invention. In addition, all examples conducted with purified mevalonate can also be conducted with unpurified material.

Example 1

Plasmid and *E. coli* Strain Construction

Genetic segments encoding mvaE (acetyl-CoA acetyltransferase/HMG-CoA reductase, GenBank No. AAG02438) and mvaS (HMG-CoA synthase, GenBank No. AAG02439) in *Enterococcus faecalis* V583 were amplified from its genomic DNA (obtained from ATCC). These segments were inserted into a vector (with pBR322 origin backbone, Ampicillin marker, lacIq, rrnB transcription termination sequences) under the control of IPTG inducible Trc promoter-lac operator to obtain plasmid pSE1 (SEQ ID NO:1).

Chemically competent *E. coli* cells of XL-1Blue strain (endA1 gyrA96(nal$^R$) thi-1 recA1 relA1 lac glnV44 F'[::Tn10 proAB$^+$ lacI$^q$ Δ(lacZ)M15] hsdR17($r_K^-$ $m_K^+$)) were transformed with plasmid pSE1 using the procedures outlined in Sambrook-Maniatis (Green, M. R.; Sambrook, J. Ed. Molecular Cloning: A Laboratory Manual, Fourth Edition, 2002) to obtain strain *E. coli*-SE1.

Example 2

Mevalonolactone Production

*E. coli*-SE1 strain was propagated in LB medium supplemented with 100 µg/liter ampicillin in 250 mL of media in a 1 liter conical flask incubated at 37° C. in an orbital shaker at 220 rpm for 10 hours reaching an OD600 of 3. This was used as an inoculum for the production in an Infors 5 lt bioreactor. 1.75 liter of production media (containing 15 g/l glucose, 7 g/l KH$_2$PO$_4$, 1 g/l NH$_4$Cl, 5 g/l yeast extract, 1 g/l citric acid, 10 mg MnSO$_4$, 2 g/l MgSO$_4$, 200 mg/l FeSO$_4$ and 10 mg/l thiamine.HCl) was combined with 250 mL of inoculum in the bioreactor. The pH was maintained at 7 with 20% NH$_4$OH. Temperature was maintained at 32° C. Air was sparged at 2 liters per minute (LPM) and agitation was maintained at 700 rpm. 10 hours after inoculation, 1 ml of 1M IPTG was added to the bioreactor. Anti-foam was added as needed. Glucose concentration was maintained around 10 g/l, by addition of 600 g/l glucose solution to the bioreactor at 2 hour intervals. The bioreactor run was stopped at 48 hours. Cells were separated from the broth by use of 0.45 micro filters to obtain clear broth. Mevalonolactone concentration was found to be 40 g/l at end of the fermentation.

Example 3

Mevalonolactone Purification

The clear broth from Example 2 was concentrated by evaporation in a rotary evaporator to a volume of 400 mL, and acidified to pH 2 by addition of 20% H$_2$SO$_4$. NaCl was added until the solution was saturated with it. Mevalonolactone was extracted into ethyl acetate by using 200 mL four times to obtain 800 mL of ethyl acetate. This was concentrated to 200 mL in a rotary evaporator. Mevalonolactone was back extracted into 150 ml 10M NaOH solution from the ethyl acetate. The acidification and ethyl extraction steps were repeated and all the ethyl acetate was evaporated to obtain mevalonolactone with purity over 95%.

Example 4

Plasmid and Cyanobacterial Strain Construction

Genetic segments encoding mvaE (acetyl-CoA acetyltransferase/HMG-CoA reductase, GenBank No. AAG02438) and mvaS (HMG-CoA synthase, GenBank No. AAG02439) in *Enterococcus faecalis* V583 are amplified from its genomic DNA (obtained from ATCC). These segments are inserted into vector MCS under the control of constitutive promoter, psbA1, to obtain plasmid pMSE1.

The construct is inserted into the Cyanobacterium *Synechococcus elongatus* strain PCC 7942 genome using plasmid pMSE1 as per manufacturer's procedures (Invitrogen, GeneArt® *Synechococcus* Protein Expression Kit, Publication No. MAN0009792, pages 16-17) to obtain strain *S. elongatus*-MSE1.

Example 5

Photosynthetic Production of Mevalonolactone

*S. elongatus*-MSE1 strain is propagated in BG-11 medium supplemented with 50 mM $NaHCO_3$ and 10 mg/l thiamine. Cells are grown in 600 mL of media in a 1 liter Roux bottle incubated at 30° C. under fluorescent light (55 µE $s^{-1}$ $m^{-2}$), which is provided by eight 86-cm 20-W fluorescent tubes placed 15 cm from the cell culture and aerated by air containing 5% $CO_2$. Daily, one-tenth the total volume of cell culture is removed from the cell culture. Then the same volume of fresh medium containing 0.5 M $NaHCO_3$ is added to cell culture. The pH of the cell culture with $NaHCO_3$ is adjusted to 7.5 with 10 N HCl every day. This is done for 10 days.

Example 6

Production of Mevalonolactone from Acetate

*E. coli*-SE1 strain was propagated in LB medium supplemented with 100 µg/liter ampicillin in 5 mL of media in a 15 ml tube incubated at 37° C. in an orbital shaker at 220 rpm for 10 hours reaching an OD600 of 3. This was used as an inoculum for the production in a 250 ml shake flask. 50 mL of production media (containing 5 g/l sodium acetate, 7 g/l $KH_2PO_4$, 1 g/l $NH_4Cl$, 5 g/l yeast extract, 1 g/l citric acid, 10 mg $MnSO_4$, 2 g/l $MgSO_4$, 200 mg/l $FeSO_4$ and 10 mg/l thiamine.HCl) was combined with 5 mL of inoculum in the shake flask. The pH was maintained at 7 with 20% $NH_4OH$. Temperature was maintained at 32° C. 10 hours after inoculation, 25 µl of 1M IPTG was added to the flask. Acetate concentration was maintained around 2 g/l by addition of 300 g/l sodium acetate solution to the shake flask at 6 hour intervals. The run was stopped at 72 hours. Cells were separated from the broth by use of 0.45 micro filters to obtain clear broth. Mevalonolactone concentration was found to be 8 g/l at end of the fermentation.

Example 7

Production of Mevalonolactone from Glycerol

*E. coli*-SE1 strain was propagated in LB medium supplemented with 100 µg/liter ampicillin in 5 mL of media in a 15 ml tube incubated at 37° C. in an orbital shaker at 220 rpm for 10 hours reaching an OD600 of 3. This was used as an inoculum for the production in a 250 ml shake flask. 50 mL of production media (containing 10 g/l glycerol, 7 g/l $KH_2PO_4$, 1 g/l $NH_4Cl$, 5 g/l yeast extract, 1 g/l citric acid, 10 mg $MnSO_4$, 2 g/l $MgSO_4$, 200 mg/l $FeSO_4$ and 10 mg/l thiamine.HCl) was combined with 5 mL of inoculum in the shake flask. The pH was maintained at 7 with 20% $NH_4OH$. Temperature was maintained at 32° C. 10 hours after inoculation, 25 µl of 1M IPTG was added to the flask. Glycerol concentration was maintained around 5 g/l by addition of 400 g/l aqueous glycerol solution to the shake flask at 6 hour intervals. The run was stopped at 72 hours. Cells were separated from the broth by use of 0.45 micro filters to obtain clear broth. Mevalonolactone concentration was found to be 15 g/l at end of the fermentation.

Example 8

Production of Mevalonolactone from Syn-Gas

Production of mevalonate from syn-gas (mixture of $CO_2$, CO and $H_2$ in various ratios) is described by Kiriukhin et al. ("Mevalonate production by engineered acetogen biocatalyst during continuous fermentation of syngas or $CO_2/H_2$ blend," *Bioprocess Biosyst. Eng.* 2014 37, 245-260), and is herein incorporated in its entirety.

Example 9

Plasmid and Yeast Strain Construction

The promoter and terminator DNA sequences were synthesized by Biobasic, Inc, Canada. Codon optimized gene sequences for the enzymes mvaE and mvaS-(A110G) from *E. faecalis* were synthesized by Biobasic. Sequences encoding mvaE under control of TDH3 promoter, and ADH1 terminator and mvaS-(A110G) under control of TEF1 promoter and ACT1 terminator, were cloned into a vector (which contains a 2 micron origin, URA3 marker and Ampicillin marker) to obtain plasmid pVS19 (SEQ ID NO:2).

Yeast *S. cerevisiae* CEN.PK2-1C (MATa; ura3-52; trp1-289; leu2-3, 112; his3Δ 1; MAL2-8$^C$; SUC2) was transformed with plasmid pVS19 using the procedures outlined in Sambrook-Maniatis (Green, M. R.; Sambrook, J. Ed. Molecular Cloning: A Laboratory Manual, Fourth Edition, 2002) to obtain stain *S. cerevisiae*-VS19.

Example 10

Production of Mevalonolactone from Sucrose

*S. cerevisiae*-VS19 strain was propagated in 5 ml of CM Glucose Broth minus Uracil (Teknova catalogue no. C8140) media in a 15 ml tube incubated at 30° C. in an orbital shaker at 220 rpm for 72 hours. Cells were separated from the broth by use of 0.45 micro filters to obtain clear broth. Mevalonolactone concentration was found to be 1.2 g/l at end of the fermentation.

Example 11

Initial Reactor Conditions

Fixed Bed Reactor Set-Up

Reactions were performed in a high pressure small scale test unit (FIG. 1) equipped with three gas lines, controlled by high accuracy mass flow controllers and one liquid feed line, delivering liquid feedstocks via a high precision pump. The unit operates with a stainless steel fixed bed reactor, externally heated with a three-zone furnace, while the exit stream of the reactor is cooled via a heat exchanger and is directed to a system of vessels for the separation and collection of the liquid and gaseous products. The reaction temperature was monitored with a thermocouple inserted in the catalytic bed. Both the liquid products and the gaseous stream were analyzed with gas chromatography.

Catalyst & Feedstock

Tests were conducted with a commercial amorphous $SiO_2/Al_2O_3$ catalyst supplied by Grace (DAVICAT SIAL 3113) and a commercial ZSM-5 ($SiO_2/Al_2O_3$ ratio 23—CBV2314) supplied by Zeolyst Inc. In both cases, the catalysts were supplied in powder form. The amorphous $SiO_2/Al_2O_3$ was used as provided. The ZSM-5 catalyst was calcined in air at 500° C. for 3 h in order to convert from the ammonium to the $H^+$-form. The sample was then crushed and sieved to a particle size of 100-180 μm prior to use. The tests were performed with 10 wt % and 20 wt % aqueous solutions of mevalonolactone, and 10 wt % dehydro-mevalonolactone (also referred to as anhydro-mevalonolactone).

Catalyst Loading

A plug of glass wool was first inserted in the reactor and after packing, the reactor was filled with the necessary catalyst amount. On top another plug of glass wool was inserted, and the reactor was then connected to the unit.

Experimental Procedure and Conditions

The mevalonolactone conversion tests were performed in the down-flow stainless steel fixed bed reactor loaded with the appropriate amount (14.3 g) of catalyst. The catalyst was pretreated in-situ at 300° C. in air for 30 min. Prior to feed introduction, the desired reaction temperature and pressure was achieved under flowing inert gas ($N_2$). Upon reaching the desired reaction conditions, the aqueous solution of mevalonolactone (10 wt % mevalonolactone) was fed to the packed tubular reactor using a high precision pump. In order to maintain the pressure, a small $N_2$ flow (50 $cm^3$/min) was co-fed with the liquid feed. The reaction was conducted at a pressure of 36 bar using a weight hourly space velocity (WHSV) of 1 $h^{-1}$ or 2 $h^{-1}$. The WHSV was calculated based on the total liquid feed (solution). Steady-state activity measurements were taken after ~2 hours time on-stream for each condition. Liquids were collected in a trap (~10° C.), while gaseous samples were collected in gas sampling bags.

Product Analysis

Analysis of gaseous products was performed on a GC equipped with two detectors (FID and TCD) and three columns (MS, Porapak N and $Al_2O_3$/KCl) in a series-bypass configuration. The liquids were analyzed on GC-MS.

TABLE 1

Reaction conditions for Example 11

| Condition | Catalyst | T [° C.] | Pressure [bar] | WHSV [$h^{-1}$] | Feed |
|---|---|---|---|---|---|
| 1 | Amorphous $SiO_2/Al_2O_3$ | 200 | 36 | 1 | 10% aq solution mevalonolactone |
| 2 | Amorphous $SiO_2/Al_2O_3$ | 300 | 36 | 1 | 10% aq solution mevalonolactone |
| 3 | Amorphous $SiO_2/Al_2O_3$ | 400 | 36 | 1 | 10% aq solution mevalonolactone |
| 4 | ZSM-5 | 200 | 36 | 1 | 10% aq solution mevalonolactone |
| 5 | ZSM-5 | 400 | 36 | 1 | 10% aq solution mevalonolactone |

The analysis of the liquid products of the reaction utilizing amorphous $SiO_2/Al_2O_3$ with GC-MS showed no presence of the feed (i.e., mevalonolactone) in the product in any of the investigated temperatures, indicating that full conversion of mevalonolactone was achieved in the conditions studied. The composition of the liquid products by GC-MS and the gaseous products as a function of temperature is presented in Tables 2 and 3 respectively.

TABLE 2

Analysis of the liquid products by GC-MS obtained over amorphous SiO2/A1203

| Conditions | 1 | 2 | | 3 | |
|---|---|---|---|---|---|
| WHSV, $h^{-1}$ | 1 | 1 | | 1 | |
| Pressure, bar | 36 | 36 | | 36 | |
| Temperature, ° C. | 200 | 300 | | 400 | |
| GC-MS analysis, area % | | Lower | Upper | | |
| Mevalonolactone | | | | | |
| Dehydromevalonic lactone | 93.4 | 20.99 | | | |
| 2-methyl-2-Propanol | 1.4 | 2.67 | | | |
| 2-methyl-1,3-Butadiene | | 1.1 | 4 | | |
| 2-methyl-3-Buten-2-ol | | 1.06 | | | 3.2 |
| 3-methyl-2-Butanone | 1.465 | 45.74 | 2.8 | | 88.945 |
| 3-methy1-3-Buten-1-ol | | 10.23 | | | |
| 2-hydroxy-Butanoic acid | | | | | 5.48 |
| 2-Butanone | | | | | 3.365 |
| Acetic acid | | 1.07 | | | 2.74 |
| Propylene Glycol | | | | | 1.68 |
| Ethyl alcohol | | 1.59 | | | |
| 1,3-Pentadiene | | 1.7 | | | |
| 2,2-dimethyl-Propanal | | 1.19 | | | |
| 1-(methylethoxy)-2-Propanol | | 1.95 | | | |
| 1-methyl-2-(1-methylethyl)-Benzene | | 1.67 | 3.15 | | |
| 1,2,4,5-tetramethyl-Benzene | | 1.54 | 6.85 | | |
| 1-methyl-4-(1-methylethyl)-Benzene | | | 6.06 | | |
| Benzene, 4-ethyl-1,2-dimethyl- | | | 3.92 | | |
| Benzene, pentamethyl- | | | 3.67 | | |
| Benzene, 1,2,3,4-tetramethyl- | | | 3.63 | | |
| Benzene, 1,2,3-trimethyl- | | | 3.48 | | |
| Benzene, 1,3-dimethyl-5-(1-methylethyl)- | | | 2.72 | | |
| Benzene, 2-ethyl-1,4-dimethyl- | | | 2.71 | | |
| Butanal, 2-methyl- | | | 2.06 | | |
| Benzene, pentamethyl- | | | 1.7 | | |
| Benzene, 4-ethyl-1,2-dimethyl- | | | 1.65 | | |
| Benzene, (1-methylethyl)- | | | 1.61 | | |
| .alpha., .beta., .beta.-Trimethylstyrene | | | 1.5 | | |
| Other* | | | 48.49 | | |
| Total | 96.625 | 94.64 | 100 | | 100 |

The main product obtained in the liquid layer was anhydro-mevalonolactone. Thus, at low temperature only dehydration reactions occur. Limited amounts of $CO_2$, along with some $C_6$ hydrocarbons, were detected in the gaseous products.

As the temperature was increased to 300° C., the liquid product separated into two distinct phases: an oily phase, forming a top layer, and an aqueous phase which resembled an emulsion and accumulated on the bottom. The two phases were separated and analyzed separately. The aqueous phase consisted mainly of 3-methyl-2-butanone, 3-methyl-3-buten-1-ol, and anhydro-mevalonolactone, demonstrating that both dehydration and ring opening reactions were taking place. The oily phase was very complex and consisted of over 150 compounds in small concentrations. The analysis shown in Table 2 represents the components detected with a concentration higher than 1.5%. The most abundant compounds in this phase were aromatic hydrocarbons with a benzene ring. A small amount of isoprene was detected in both the oily and the aqueous phase at 300° C. The gaseous product (Table 3) showed increased $CO_2$ production (higher extent of severe cracking reactions) and small amounts of light hydrocarbons.

When the temperature was raised to 400° C., the liquid product turned back to a homogeneous one phase product, with an emulsion-like texture. In this case, no anhydromevalonolactone was detected, and the major product was 3-methyl-2-butanone. A significant amount of light alkanes and olefins, ranging from $C_1$ to $C_5$ were also produced, indicating that at such high temperature (400° C.), extensive decarboxylation and cracking of the lactone feed occurred.

TABLE 3

Analysis of the gaseous products obtained over amorphous $SiO_2/Al_2O_3$

| Conditions | 1 | 2 | 3 |
|---|---|---|---|
| WHSV, $h^{-1}$ | 1 | 1 | 1 |
| Pressure, bar | 36 | 36 | 36 |
| Temperature, ° C. | 200 | 300 | 400 |
| GC analysis vol % | | | |
| Methane | | | 0.234 |
| Ethane | | | 0.045 |
| Ethylene | | | 0.043 |
| Propane | | | 0.04 |
| Propylene | | 0.024 | 0.22 |
| Isobutane | | | 0.106 |
| n-butane | | | 0.009 |
| 1-butene | | 0.009 | 0.071 |
| Isobutylene | | | 0.035 |
| Cis-2-butene | 0.281 | 0.75 | 1.212 |
| Isopentane | | 0.005 | 0.037 |
| n-pentane | | | 0.038 |
| $C_{5+}$ | 0.01 | 0.142 | 1.037 |
| $C_{6+}$ | 1.894 | 1.621 | 0.183 |
| $CO_2$ | 4.354 | 10.916 | 9.744 |
| CO | | 0.124 | 0.317 |
| $N_2$ | 95.613 | 88.865 | 91.398 |
| Total | 102.209 | 102.495 | 104.896 |

Catalytic Results with ZSM-5

As in the case of amorphous $SiO_2/Al_2O_3$, unconverted mevalonolactone was not detected in the liquid product of any of the investigated temperatures with ZSM-5 catalysis. This indicated that full conversion of mevalonolactone was also achieved under the conditions studied with ZSM-5. The composition of the liquid products by GC-MS and the gaseous products as a function of temperature over ZSM-5 is presented in Tables 4 and 5 respectively.

At 200° C., the liquid product of the reaction was an emulsion-like homogeneous solution. The main products obtained are the anhydrous form of mevalonolactone and 3-methyl-2-butanone. Limited amounts of $CO_2$ were detected in the gas products. Compared to the amorphous silica-alumina, where only dehydrated mevalonolactone was observed at 200° C., the much more acidic ZSM-5 catalyst not only catalyzed dehydration, but also decarboxylation.

At 400° C., the liquid product separated into two distinct phases: an oily phase, forming a top layer, and an aqueous emulsion-like phase. The two phases were again separated and analyzed separately. The aqueous phase consisted mainly of acetic/propanoic acid, acetone, and toluene. In contrast to 200° C. and the results with amorphous silica alumina, no 3-methyl-2-butanone was observed. This indicates the occurrence of extensive decarboxylation/cracking reactions. The oily phase was comprised of aromatic compounds, such as p-xylene, toluene, 1,2,3-trimethyl-benzene, and 1-ethyl-2-methyl-benzene. These aromatics are probably a result of oligomerization reactions of olefins which form as intermediates over ZSM-5. $CO_2$ and small amounts of light hydrocarbons (alkanes/alkenes) were detected in the gas phase, as shown in Table 5.

TABLE 4

Analysis of liquid products by GC-MS obtained over ZSM-5

| Conditions | 4 | 5 | |
|---|---|---|---|
| WHSV, $h^{-1}$ | 1 | 1 | |
| Pressure, bar | 36 | 36 | |
| Temperature, ° C. | 200 | 400 | |
| GC-MS analysis, area % | | Lower | Upper |
| Mevalonolactone Dehydromevalonic lactone | 66.15 | | |
| No matches found | 0.31 | 6.04 | |
| Ethyl alcohol | 0.28 | 3.10 | |
| Butane | 0.55 | | |
| 2-Propanol, 2-methyl- | 3.28 | | |
| Propanal, 2,2-dimethyl- | 0.56 | | |
| 2-Butanone | 0.32 | | |
| Butanal, 2,2-dimethyl- | 0.3 | | |
| 2-Butanone, 3-methyl- | 15.75 | | |
| Acetone | | 23.10 | |
| 2-Butanone | | 5.44 | |
| Acetic acid | 0.35 | 40.50 | |
| Propanoic acid | | 5.07 | |
| Isopropyl Alcohol | | 4.62 | |
| 2-Propanol, 1-(1-methylethoxy)- | | 5.10 | |
| p-Xylene | 3.79 | | 22.7 |
| o-xylene | 1.11 | | |
| Benzene, 1,2,3-trimethyl- | | | 13.34 |
| Benzene, 1-ethyl-2-methyl- | 1.96 | | 12.58 |
| Toluene | 1.96 | 7.03 | 11.39 |
| Benzene, 1,3-dimethyl- | | | 6.92 |
| Benzene, 4-ethyl-1,2-dimethyl- | | | 3.45 |
| 2-Tolyloxirane | | | 1.42 |
| Benzene, 1,3,5-trimethyl- | 2.59 | | |
| Benzene, 1-methyl-2-(1-methylethyl | 0.73 | | |
| Benzene, 1-methyl-3-propyl- | | | 1.21 |
| Naphthalene, 1-methyl- | | | 1.16 |
| Naphthalene, 2,7-dimethyl- | | | 1.07 |
| 1-Phenyl-1-butene | | | 1 |
| Benzene, (1-methyl-1-butenyl)- | | | 0.89 |
| Benzene, 1-methyl-4-(1-methylethyl | | | 0.86 |
| Benzene, 1,3-diethyl- | | | 0.86 |
| Benzene, 2-butenyl- | | | 0.69 |
| Benzene, propyl- | | | 0.6 |
| Naphthalene, 1,2,3,4-tetrahydro-6-methyl- | | | 1.54 |
| Other* | | | 19.32 |
| TOTAL | 100 | 100 | 100 |

TABLE 5

Analysis of gaseous products obtained over ZSM-5

| Conditions | 4 | 5 |
|---|---|---|
| WHSV, $h^{-1}$ | 1 | 1 |
| Pressure, bar | 36 | 36 |
| Temperature, ° C. | 200 | 400 |

TABLE 5-continued

Analysis of gaseous products obtained over ZSM-5

| Conditions | 4 | 5 |
|---|---|---|
| GC analysis, vol % | | |
| Hydrogen | | 0.06 |
| Methane | | |
| Ethane | | |
| Ethylene | | |
| Propane | | 0.46 |
| Propylene | | 0.06 |
| Isobutane | 0.02 | 0.68 |
| n-butane | | 0.14 |
| 1-butene | | |
| Isobutylene | 1.15 | 0.05 |
| Trans-2-butene | | 0.02 |
| Cis-2-butene | | |
| 1,3-butadiene | | |
| Isopentane | | 0.22 |
| n-pentane | | |
| 1-pentylene | | |
| $C_{5+}/C_{6+}$ | 0.55 | 0.34 |
| $CO_2$ | 8.58 | 4.65(??) |
| CO | | 0.47 |
| $N_2$ | 93.26 | 90.20 |
| Total | 103.55 | 97.35 |

Example 12

Effect of Temperature Over Amorphous $SiO_2/Al_2O_3$

The reactions in Example 12 were run in an analogous procedure to that described in Example 11.

TABLE 6

Reaction Conditions in Examples 12 and 13

| Condition | Catalyst | T [° C.] | Pressure [bar] | WHSV [h$^{-1}$] | Feed |
|---|---|---|---|---|---|
| 1 | Amorphous $SiO_2/Al_2O_3$ | 275 | 36 | 1 | 10% aq solution dehydro-mevalonolactone (product of reaction at 200° C. with ASA) |
| 2 | Amorphous $SiO_2/Al_2O_3$ | 325 | 36 | 1 | 10% aq solution mevalonolactone |
| 3 | Amorphous $SiO_2/Al_2O_3$ | 325 | 36 | 2 | 10% aq solution mevalonolactone |
| 4 | Amorphous $SiO_2/Al_2O_3$ | 325 | 36 | 1 | 20% aq solution mevalonolactone |

The composition of the liquid products by GC-MS and the gaseous products at 275° C. and 325° C. (conditions 1 and 2 of Table 6) are presented in Tables 7 and 8, respectively. The results for the previously investigated temperatures (200, 300 and 400° C.) are also presented for comparison reasons. The analysis of the liquid products of the reaction with GC-MS showed no presence of the feed (i.e., mevalonolactone) in the product in any of the investigated temperatures, indicating that full conversion of mevalonolactone was achieved in the conditions studied.

TABLE 7

Analysis of liquid products by GC-MS obtained over amorphous $SiO_2/Al_2O_3$ at experiments with constant WHSV and pressure and varying temperature

| WHSV, h$^{-1}$ | 1 | 1 | 1 | 1 | 1 |
|---|---|---|---|---|---|
| Pressure, bar | 36 | 36 | 36 | 36 | 36 |
| Temperature, ° C. | 200 | 275 | 300 | 325 | 400 |
| Visual inspection | | | Lower | Upper | |
| GC-MS analysis, area % | | | | | |
| Mevalonolactone | | | | | |
| Dehydromevalonic lactone | 93.4 | | 20.99 | 17.55 | |
| 2-methyl-2-Propanol | 1.4 | | 2.67 | 7.1 | |
| 2-methyl-1,3-Butadiene | | | *1.1* | *4* | *5.42* |
| 2-methyl-3-Buten-2-ol | 1.06 | | 3.2 | 3.2 | |
| 3-methyl-2-Butanone | 1.465 | 78.05 | 45.74 | 2.8 | 44.51 | 88.945 |
| 3-methyl-3-Buten-1-ol | | | 10.23 | 2.31 | |
| 2-hydroxy-Butanoic acid | | | | | 5.48 |
| 2-Butanone | | | | | 3.365 |
| Acetic acid | | | 1.07 | | 2.74 |
| Propylene Glycol | | | | 4.83 | 1.68 |
| Ethyl alcohol | | 3.83 | 1.59 | 2.56 | |
| 1,3-Pentadiene | | | 1.7 | | |
| 2,2-dimethyl-Propanal | | 4.04 | 1.19 | | |
| 1-(methylethoxy)-2-Propanol | | | 1.95 | | |
| 1-Butanol, 4-methoxy- | | 3.01 | | | |
| Ethanol, 2-(2-methoxyethoxy)- | | | | | 3.45 |
| 1-methyl-2-(1-methylethyl)-Benzene | | | 1.67 | 3.15 | |
| 1,2,4,5-tetramethyl-Benzene | | | 1.54 | 6.85 | |

TABLE 7-continued

Analysis of liquid products by GC-MS obtained over amorphous $SiO_2/Al_2O_3$ at experiments with constant WHSV and pressure and varying temperature

| | | | | | |
|---|---|---|---|---|---|
| 1-methyl-4-(1-methylethyl)-Benzene | | 6.06 | | | |
| Benzene, 4-ethyl-1,2-dimethyl- | | 3.92 | | | |
| Benzene, pentamethyl- | | 3.67 | | | |
| Benzene, 1,2,3,4-tetramethyl- | | 3.63 | | | |
| Benzene, 1,2,3-trimethyl- | | 3.48 | | | |
| Benzene, 1,3-dimethyl-5-(1-methylethyl)- | | 2.72 | | | |
| Benzene, 2-ethyl-1,4-dimethyl- | | 2.71 | | | |
| Butanal, 2-methyl- | | 2.06 | | | |
| Benzene, pentamethyl- | | 1.7 | | | |
| Benzene, 4-ethyl-1,2-dimethyl- | | 1.65 | | | |
| Benzene, (1-methylethyl)- | | 1.61 | | | |
| .alpha.,.beta.,.beta.-Trimethylstyrene | | 1.5 | | | |
| 1.3Cyclohexadiene, 1-methyl-4-(1methylethyl) | | | | 3.45 | |
| Other | | 11.06 | | 48.49 | 5.75 |
| Total | 96.625 | 99.99 | 94.64 | 100 | 100.13 | 100 |

TABLE 8

Analysis of gaseous products obtained over amorphous $SiO_2/Al_2O_3$ at experiments with constant WHSV and pressure and varying temperature

| WHSV, $h^{-1}$ | 1 | 1 | 1 | 1 | 1 |
|---|---|---|---|---|---|
| Pressure, bar | 36 | 36 | 36 | 36 | 36 |
| Temperature, °C. | 200 | 275 | 300 | 325 | 400 |
| GC analysis, vol % | | | | | |
| Methane | | | | | 0.234 |
| Ethane | | | | | 0.045 |
| Ethylene | | | | | 0.043 |
| Propane | | | | | 0.04 |
| Propylene | | 0.006 | 0.024 | 0.007 | 0.22 |
| Isobutane | | | | 0.004 | 0.106 |
| n-butane | | | | | 0.009 |
| 1-butene | | | 0.009 | 0.004 | 0.071 |
| Isobutylene | | | | | 0.035 |
| Cis-2-butene | | | | | |
| Isopentane | | | | | |
| n-pentane | | | | | |
| Cis-2-butene | 0.281 | 0.31 | 0.75 | 0.280 | 1.212 |
| Isopentane | | | 0.005 | 0.003 | 0.037 |
| n-pentane | | | | | 0.038 |
| $C_{5+}$ | 0.01 | 0.033 | 0.142 | 0.045 | 1.037 |
| $C_{6+}$ | 1.894 | 0.811 | 1.621 | 1.260 | 0.183 |
| $CO_2$ | 4.354 | 2.975 | 10.916 | 3.053 | 9.744 |
| CO | | 0.05 | 0.124 | 0.063 | 0.317 |
| $N_2$ | 95.613 | 97.385 | 88.865 | 97.151 | 91.398 |
| Total | 102.209 | 101.654 | 102.495 | 101.973 | 104.896 |

The main product obtained at 275° C. was 3-methyl-2-butanone, while no isoprene was formed. At 325° C., isoprene was formed in measurable amounts, together with 3-methyl-2-butanone, 2-methyl-2-propanol, and dehydro-mevalonolactone. The presence of the anhydrous form was unexpected at 325° C., as dehydration seemed to be completed even at 275° C. This inconsistency however can be explained by the fact that the feed for the experiment at 275° C. was dehydro-mevalonolactone (obtained at a previous experiment with ASA at 200° C.), while the experiment at 325° C. was conducted with a mixture of dehydro-mevalonolactone and fresh feed (i.e., mevalonolactone).

The gaseous product (Table 8) does not show a constant trend in $CO_2$ emissions with temperature, which can again be attributed to the different feeds used for the investigated conditions. It is clear however, that the concentration of light hydrocarbons increased with temperature, indicative of a higher extent of cracking reactions.

Since the optimum results in terms of isoprene formation were obtained at 325° C., this temperature was selected for further investigation of the effect of WHSV and feed dilution, in the decarboxylation of mevalonolactone over amorphous $SiO_2/Al_2O_3$.

Example 13

Effect of Feed Concentration and WHSV Over Amorphous $SiO_2/Al_2O_3$

An analogous procedure to Example 11 was used. The reaction conditions are described in Table 6. Tables 9 and 10 present the composition of the liquid and gaseous products, respectively, obtained at a higher WHSV and with an increased mevalonolactone concentration in the feed. The reference conditions (WHSV=1 $h^{-1}$, 10% aq solution) are also presented in the first column for comparison reasons.

However, we see a clear increase in the production of isoprene, indicating that it is an intermediate product, and therefore favored at lower residence times. An increase was also observed in the concentration of 2-methyl-2-propanol, while the formation of 3-methyl-2-butanone seems unaffected.

Major changes were detected when the feed concentration of mevalonolactone was increased from 10 to 20 wt %. An order of magnitude increase in isoprene formation was recorded with the higher concentration feed. The only other major product with the 20 wt % mevalonolactone feed was 3-methyl-2-butanone. These results suggest that in order to increase the amount of isoprene, higher space velocities and denser feeds should be employed.

TABLE 9

Analysis of liquid products by GC-MS obtained over amorphous $SiO_2/Al_2O_3$ at experiments with varying feed composition and WHSV at 325° C.

| WHSV, $h^{-1}$ | 1 | 2 | 1 |
|---|---|---|---|
| Pressure, bar | 36 | 36 | 36 |
| Temperature, ° C. | 325 | 325 | 325 |
| Concentration of aq solution of mevalonolactone, % | 10 | 10 | 20 |
| GC-MS analysis, area % | | | |
| Mevalonolactone | | | |
| Dehydromevalonic lactone | 17.55 | | |
| 2-methyl-2-Propanol | 7.1 | 14.807 | |
| 2-methyl-1,3-Butadiene | 5.42 | 8.238 | 54.307 |
| 2-methyl-3-Buten-2-ol | 3.2 | | |
| 3-methyl-2-Butanone | 44.51 | 46.507 | 33.232 |
| 3-methyl-3-Buten-1-ol | 2.31 | 4.982 | |
| Ethyl alcohol | 2.56 | 5.038 | |
| 2,2-dimethyl-Propanal | | 8.628 | |
| Ethanol, 2-(2-methoxyethoxy)- | 3.45 | | |
| 1.3Cyclohexadiene, 1-methyl-4-(1methylethyl) | 3.45 | | |
| Propylene Glycol | 4.83 | | |
| Other | 5.75 | 11.801 | 12.462 |
| Total | 100.13 | 100.00 | 100.00 |

TABLE 10

Analysis of gaseous products obtained over amorphous $SiO_2/Al_2O_3$ at experiments with varying feed composition and WHSV at 325° C.

| WHSV, $h^{-1}$ | 1 | 2 | 1 |
|---|---|---|---|
| Pressure, bar | 36 | 36 | 36 |
| Temperature, ° C. | 325 | 325 | 325 |
| Concentration of aq solution of mevalonolactone, % | 10 | 10 | 20 |
| GC analysis, vol % | | | |
| Ethylene | | 0.007 | 0.008 |
| Propane | | | |
| Propylene | 0.007 | 0.012 | 0.01 |
| Isobutane | 0.004 | | |
| 1-butene | 0.004 | 0.005 | 0.005 |
| Isobutylene | | 1.601 | 1.253 |
| Cis-2-butene | 0.280 | | |
| Isopentane | 0.003 | 0.004 | 0.004 |
| $C_{5+}$ | 0.045 | 0.092 | 0.104 |
| $C_{6+}$ | 1.260 | 1.903 | 2.593 |
| $CO_2$ | 3.053 | 11.21 | 12.028 |
| CO | 0.063 | 0.154 | 0.128 |
| $N_2$ | 97.151 | 88.131 | 85.832 |
| Total | 101.973 | 103.119 | 101.965 |

Further Analysis on Experiment with 20% Aq Solution of Mevalonolactone

As discussed above, the experiment performed with 20% aqueous solution of mevalonolactone over amorphous $SiO_2/Al_2O_3$ at 325° C. showed a high percentage of isoprene in the liquid product as % area of isoprene to the total product area peaks in the GC-MS analysis. As this condition demonstrated the most promising results in terms of isoprene formation, we performed further analysis of the liquid product sample in an effort to quantify the amount of isoprene. The first step comprised of measuring the amount of water in the liquid product with the Karl-Fischer method (ASTM D6304). The water was found to be ~94 wt % in the liquid product. This indicated that the main product of the reaction was water and the concentration of organics in the liquid product sample was <6 wt %. Furthermore, we attempted to perform a semi-quantitative analysis using isoprene standard of the GC-MS to measure the actual concentration of the desired product. These results pointed out that the actual concentration of isoprene is probably <3 wt %, with the rest being 3-methyl-2-butanone and other unidentified components.

Example 14

Synthesis of Isoprene

The mevalonolactone conversion to isoprene is performed in the down-flow stainless steel fixed bed reactor loaded with amorphous $SiO_2/Al_2O_3$ catalyst, according to Example 11. The catalyst is pretreated in-situ at 300° C. in air for 30 min. Prior to feed introduction, the desired reaction temperature, 325° C., and pressure, 36 bar, is achieved under flowing inert gas ($N_2$). Upon reaching the desired reaction conditions, the aqueous solution of mevalonolactone (aq. 600 g mevalonolactone/L) is fed to the packed tubular reactor using a high precision pump. In order to maintain the pressure, a small $N_2$ flow (50 $cm^3$/min) is co-fed with the liquid feed. The reaction is conducted at a pressure of 36 bar using a weight hourly space velocity (WHSV) of 2 $h^{-1}$. The WHSV is calculated based on the total liquid feed (solution). Steady-state activity measurements are taken after ~2 hours time on-stream. Liquids are collected in a trap (~10° C.), while gaseous samples are collected in gas sampling bags.

Additional Experiments Varying Feed Concentration and Space Velocity

Using the above described the set-up, 14.3 gm of catalyst $SiO_2/Al_2O_3$(DAVICAT SIAL 3113 supplied by Grace in powder form and used as such) is loaded in the fixed bed reactor and pretreated in-situ at 300° C. in air for 30 mins. Aqueous solutions of pure Mevalonolactone obtained from Example 11 are pumped through the reactor at different conditions as summarized in Table 11. The major product in each experiment is isoprene, with 3-methyl-2-butanone as a side product.

TABLE 11

Additional Experiments varying feed concentration and space velocity

| Condition | Temperature (° C.) | Feed concentration (%) | Space velocity (WHSV $h^{-1}$) | Pressure (bar) |
|---|---|---|---|---|
| 1 | 325 | 30% | 1 | 36 |
| 2 | 325 | 50% | 1 | 36 |
| 3 | 325 | 70% | 1 | 36 |
| 4 | 325 | 30% | 2 | 36 |
| 5 | 325 | 50% | 2 | 36 |
| 6 | 325 | 70% | 2 | 36 |
| 7 | 325 | 30% | 3 | 36 |
| 8 | 325 | 50% | 3 | 36 |
| 9 | 325 | 70% | 3 | 36 |
| 10 | 325 | 10% | 3 | 36 |

Example 15

Synthesis of Substituted Aromatics

The mevalonolactone conversion to substituted aromatics is performed in the down-flow stainless steel fixed bed reactor loaded with amorphous ZSM-5 catalyst, as described in Example 11. The catalyst is pretreated in-situ at 300° C. in air for 30 min. Prior to loading the ZSM-5 catalyst is calcined in air at 500° C. for 3 hours to concert the catalyst from the ammonium to $H^+$ form. The sample is crushed and sieved to a particle size of 100-180 μm prior to use. Prior to feed introduction, the desired reaction temperature (250° C., 300° C., 350° C.), and pressure (36 bar), is achieved under flowing inert gas ($N_2$). Upon reaching the desired reaction conditions, the aqueous solution of mevalonolactone (aq. 10% mevalonolactone) is fed to the packed tubular reactor using a high precision pump. In order to maintain the pressure, a small $N_2$ flow (50 $cm^3$/min) is co-fed with the liquid feed. The reaction is conducted at a pressure of 36 bar using a weight hourly space velocity (WHSV) of 1 $h^{-1}$. The WHSV is calculated based on the total liquid feed (solution). Steady-state activity measurements are taken after ~2 hours time on-stream. Liquids are collected in a trap (~10° C.), while gaseous samples are collected in gas sampling bags. The products are a mixture of aromatics and 3-methyl-2-butanone, as analyzed by liquid and gas chromatography

Example 16

Synthesis of Anhydro-Mevalonolactone

The mevalonolactone conversion to anhydro-mevalonolactone is performed in the down-flow stainless steel fixed bed reactor loaded with amorphous ZSM-5 catalyst, as described in Example 11. The catalyst is pretreated in-situ at 300° C. in air for 30 min. Prior to loading the ZSM-5 catalyst is calcined in air at 500° C. for 3 hours to convert the catalyst from the ammonium to $H^+$ form. The sample is crushed and sieved to a particle size of 100-180 μm prior to use. Prior to feed introduction, the desired reaction temperature (70° C., 100° C., 121° C., 150° C.), and pressure (36 bar), is achieved under flowing inert gas ($N_2$). Upon reaching the desired reaction conditions, the aqueous solution of mevalonolactone (aq. 10% mevalonolactone) is fed to the packed tubular reactor using a high precision pump. In order to maintain the pressure, a small $N_2$ flow (50 $cm^3$/min) is co-fed with the liquid feed. The reaction is conducted at a pressure of 36 bar using a weight hourly space velocity (WHSV) of 1 $h^{-1}$. The WHSV is calculated based on the total liquid feed (solution). Steady-state activity measurements are taken after ~2 hours on-stream. Liquids are collected in a trap (~10° C.), while gaseous samples are collected in gas sampling bags. The major product is anhydro-mevalonolactone, as analyzed by liquid and gas chromatography

Example 17

Synthesis of Anhydro-Mevalonolactone

An acetoaceyl-CoA pool is generated by *E. coli* endogenously by enzyme acetyl-CoA acetyltransferase AtoB. First HMG-CoA synthase (mvaS or hmgS) and HMG-CoA reductase (mvaE or hmgR) are cloned to provide a route for the production of mevalonate from this pool. Additionally to maximize mevalonate flux, the Protein-Protein BasicLocal Alignment Search Tool (BlastP) is used to identify mvaS and mvaE from various organisms, such as *Enterococcus faecalis, Staphylococcusaureus, Lactobacillus casei, Methanococcus maripaludis*, and *Methanococcus voltae*. Combinatorial tests are used to identify the optimum set of mvaS and mvaE for mevalonate production. To scale up the production of mevalonate, the *E. coli* strain carrying genes from *L. casei* are fermented in a 1.3-Lbioreactor. To prepare anhydro-mevalonolactone, a solid acid catalyst is added directly to the fermentation broth and heated to reflux to catalyze the dehydration of mevalonate. The resulting anhydro-mevalonolactone is isolated by solvent extraction using chloroform. The combined organic phases are concentrated in vacuo to produce crude product.

Example 18

Synthesis of Anhydro-Mevalonolactone with p-Toluene Sulfonic Acid 10 gm Mevalonolactone (obtained in Example 2) was refluxed in presence of 1 gm of p-toluene sulfonic acid in toluene for 10 hrs. We observed a yield of 85% of anhydro-mevalonolactone. The product was washed with saturated $NaHCO_3$ and passed through silica gel plug to obtain anhydro-mevalonolactone ($^1H$ NMR) with >95% purity.

Example 19

Synthesis of Anhydro-Mevalonolactone with Samarium Acetate 200 mg Mevalonolactone (obtained in Example 2) was bubbled with Argon gas for 30 mins in a 1 mL vial, and 5 mg samarium acetate was added under an Argon gas flow. The vial was sealed and put in a shaker at 150° C. for 48 hours. Anhydro-mevalonolactone was obtained, as verified by NMR.

Example 20

Synthesis of Anhydro-Mevalonolactone with Ferric Chloride 200 mg Mevalonolactone (obtained in Example 2) was bubbled with Argon gas for 30 mins in a 1 mL vial, and 4 mg $FeCl_3$ was added under an Argon gas flow. The vial was sealed and put in a shaker at 150° C. for 48 hours. Anhydro-mevalonolactone was obtained, as verified by NMR.

Example 21

Synthesis of Anhydro-Mevalonolactone with Amberlyst® 35

500 mg Mevalonolactone (obtained in Example 2) was dissolved in 10 mL water and distributed equally into 10 vials. To each vial, 63 mg of Amberlyst® 35-wet (obtained from Dow) was added. After sealing the vials and pressuring them to 65 psi, five vials were heated to 90° C. and 5 vials were heated to 150° C. 100 μl of samples were drawn at various time intervals, quenched and diluted with water and analyzed via LC-MS. Anhydro-mevalonolactone was the only major product formed, as highlighted in Table 12.

TABLE 12

Analysis of anhydro-mevalonolactone formation with Amberlyst® 35

| Time (hr) | Dehydro-mevalonolactone (Area under curve, arb. Units) | |
| --- | --- | --- |
| | 90° C. | 150° C. |
| 1 | 15,077 | 49,471 |
| 4 | 16,288 | 58,455 |
| 8 | 25,710 | 58,300 |
| 12 | 26,260 | 70,951 |
| 24 | 39,171 | 72,303 |
| 48 | 49,669 | 69,681 |

Example 22

Ethenolysis of Anhydro-Mevalonolactone

An 1 L glass reactor composed of thick wall glass is charged under nitrogen or argon with an appropriate solvent, such as dichloromethane or dichloroethane (500 mL), dehydro-mevalonolactone (0.86 mol), and a Grubbs ruthenium metathesis catalyst (0.01-1.0 mol %). After stirring for 10-60 min under nitrogen, the vessel is pressurized with 150 psi of ethylene gas and the reaction is stirred at 40° C. over a period of up to 24 hours, or until process monitoring indicates that the reaction is complete. The unused ethylene is then removed and recovered, and the reaction vessel is opened to the atmosphere. Following removal of the solvent, the crude product is purified.

Example 23

Ethenolysis of 5-hydroxy-3-methyl-2-(E)-pentenoic acid

A 1 L glass reactor composed of thick wall glass is charged under nitrogen or argon with an appropriate solvent, such as dichloromethane or dichloroethane (500 mL), 5-hydroxy-3-methyl-2-(E)-pentenoic acid (0.86 mol), and a Grubbs ruthenium metathesis catalyst (0.01-1.0 mol %). After stirring for 10-60 min under nitrogen, the vessel is pressurized with 150 psi of ethylene gas and the reaction is stirred at 40° C. over a period of up to 24 hours, or until process monitoring indicates that the reaction is complete. The unused ethylene is then removed and recovered, and the reaction vessel is opened to the atmosphere. The solution is treated with aqueous sodium hydroxide (300-500 mL, 1-5 M solution) and the aqueous layer is extracted twice with the reaction solvent. The aqueous layer is then acidified to pH 0-2, and extracted with dichloromethane or diethyl ether (5×100 mL). Following removal of the solvent, the crude product is purified.

Example 24

Methyl Ester of Anhydro-Mevalonolactone

Amberlyst® resin is added to a solution of anhydro-mevalonolactone in methanol, and the slurry is heated to reflux. After 24 h, the reaction is cooled to room temperature, filtered and concentrated in vacuo to provide crude product, which is used in further reactions without purification.

Example 25

Ethenolysis of the methyl ester of 5-hydroxy-3-methyl-2-(Z)-pentenoic acid

An 1 L glass reactor composed of thick wall glass is charged under nitrogen or argon with an appropriate solvent, such as dichloromethane or dichloroethane, the methyl ester of 5-hydroxy-3-methyl-2-(Z)-pentenoic acid from Example 24, and a Grubbs ruthenium metathesis catalyst (0.01-1.0 mol %). After stirring for 10-60 min under nitrogen, the vessel is pressurized with 150 psi of ethylene gas and the reaction is stirred at 40° C. over a period of up to 24 hours, or until process monitoring indicates that the reaction is complete. The unused ethylene is then removed and recovered, and the reaction vessel is opened to the atmosphere. Following removal of the solvent, the crude product is purified.

Example 26

Ethyl Ester of Anhydro-Mevalonolactone

Amberlyst® resin is added to a solution of anhydro-mevalonolactone in ethanol, and the slurry is heated to reflux. After 24 h, the reaction is cooled to room temperature, filtered and concentrated in vacuo to provide crude product, which is used in further reactions without purification.

Example 27

Ethenolysis of the ethyl ester of 5-hydroxy-3-methyl-2-(Z)-pentenoic acid

An 1 L glass reactor composed of thick wall glass is charged under nitrogen or argon with an appropriate solvent, such as dichloromethane or dichloroethane, the ethyl ester of 5-hydroxy-3-methyl-2-(Z)-pentenoic acid from Example 26, and a Grubbs ruthenium metathesis catalyst (0.01-1.0 mol %). After stirring for 10-60 min under nitrogen, the vessel is pressurized with 150 psi of ethylene gas and the reaction is stirred at 40° C. over a period of up to 24 hours, or until process monitoring indicates that the reaction is complete. The unused ethylene is then removed and recovered, and the reaction vessel is opened to the atmosphere. Following removal of the solvent, the crude product is purified.

Example 28

Glycerol Ester of Anhydro-Mevalonolactone

Amberlyst® resin is added to a solution of anhydro-mevalonolactone in glycerol, and the slurry is heated to reflux. After 24 h, the reaction is cooled to room temperature, filtered and concentrated in vacuo to provide crude product, which is used in further reactions without purification.

Example 29

Ethenolysis of the glycerol ester of 5-hydroxy-3-methyl-2-(Z)-pentenoic acid

An 1 L glass reactor composed of thick wall glass is charged under nitrogen or argon with an appropriate solvent, such as dichloromethane or dichloroethane, the glycerol ester of 5-hydroxy-3-methyl-2-(Z)-pentenoic acid from Example 28, and a Grubbs ruthenium metathesis catalyst (0.01-1.0 mol %). After stirring for 10-60 min under nitrogen, the vessel is pressurized with 150 psi of ethylene gas and the reaction is stirred at 40° C. over a period of up to 24 hours, or until process monitoring indicates that the reaction is complete. The unused ethylene is then removed and recovered, and the reaction vessel is opened to the atmosphere. Following removal of the solvent, the crude product is purified.

Example 30

Methyl ester of
5-hydroxy-3-methyl-2-(E)-pentenoic acid

Amberlyst® resin is added to a solution of 5-hydroxy-3-methyl-2-(E)-pentenoic acid in methanol, and the slurry is heated to reflux. After 24 h, the reaction is cooled to room temperature, filtered and concentrated in vacuo to provide crude product, which is used in further reactions without purification.

Example 31

Ethenolysis of the methyl ester of
5-hydroxy-3-methyl-2-(E)-pentenoic acid

An 1 L glass reactor composed of thick wall glass is charged under nitrogen or argon with an appropriate solvent, such as dichloromethane or dichloroethane, the methyl ester of 5-hydroxy-3-methyl-2-(E)-pentenoic acid from Example 30, and a Grubbs ruthenium metathesis catalyst (0.01-1.0 mol %). After stirring for 10-60 min under nitrogen, the vessel is pressurized with 150 psi of ethylene gas and the reaction is stirred at 40° C. over a period of up to 24 hours, or until process monitoring indicates that the reaction is complete. The unused ethylene is then removed and recovered, and the reaction vessel is opened to the atmosphere. Following removal of the solvent, the crude product is purified.

Example 32

Ethyl ester of 5-hydroxy-3-methyl-2-(E)-pentenoic acid

Amberlyst® resin is added to a solution of 5-hydroxy-3-methyl-2-(E)-pentenoic acid in ethanol, and the slurry is heated to reflux. After 24 h, the reaction is cooled to room temperature, filtered and concentrated in vacuo to provide crude product, which is used in further reactions without purification.

Example 33

Ethenolysis of the ethyl ester of
5-hydroxy-3-methyl-2-(E)-pentenoic acid

An 1 L glass reactor composed of thick wall glass is charged under nitrogen or argon with an appropriate solvent, such as dichloromethane or dichloroethane, the ethyl ester of 5-hydroxy-3-methyl-2-(E)-pentenoic acid from Example 32, and a Grubbs ruthenium metathesis catalyst (0.01-1.0 mol %). After stirring for 10-60 min under nitrogen, the vessel is pressurized with 150 psi of ethylene gas and the reaction is stirred at 40° C. over a period of up to 24 hours, or until process monitoring indicates that the reaction is complete. The unused ethylene is then removed and recovered, and the reaction vessel is opened to the atmosphere. Following removal of the solvent, the crude product is purified.

Example 34

Glycerol ester of
5-hydroxy-3-methyl-2-(E)-pentenoic acid

Amberlyst® resin is added to a solution of 5-hydroxy-3-methyl-2-(E)-pentenoic acid in glycerol, and the slurry is heated to reflux. After 24 h, the reaction is cooled to room temperature, filtered and concentrated in vacuo to provide crude product, which is used in further reactions without purification.

Example 35

Ethenolysis of the glycerol ester of
5-hydroxy-3-methyl-2-(E)-pentenoic acid

An 1 L glass reactor composed of thick wall glass is charged under nitrogen or argon with an appropriate solvent, such as dichloromethane or dichloroethane, the glycerol ester of 5-hydroxy-3-methyl-2-(E)-pentenoic acid from Example 34, and a Grubbs ruthenium metathesis catalyst (0.01-1.0 mol %). After stirring for 10-60 min under nitrogen, the vessel is pressurized with 150 psi of ethylene gas and the reaction is stirred at 40° C. over a period of up to 24 hours, or until process monitoring indicates that the reaction is complete. The unused ethylene is then removed and recovered, and the reaction vessel is opened to the atmosphere. Following removal of the solvent, the crude product is purified.

Example 36

Highly Selective Production of Isoprene and
Methyl Vinyl Ketone with Silica Catalyst A small volume fixed bed reactor was loaded with 1 gram of Davisil Grade 62 silica gel and heated to a temperature of 250 C with 1.4 sccm of nitrogen carrier gas and 2.5 uL/min flow of 20 wt % mevalonolactone in water injected via a coaxial injection. In addition, a post-reactor vapor trap held at 60-70 C is used to trap water and dehydrated mevalonolactone to prevent contamination of the in-line GC-FID used or analysis. Under these conditions, the area fraction of isoprene as analyzed using in-line GC-FID is 91% with 7% of the peak area identified as methyl vinyl ketone.

Based on peak area analysis as compared to a model stream of a molar equivalent flow of isoprene conversion is greater than 69% showing a minimum overall yield of 61% (i.e. 0.61 moles of isoprene per mole of mevalonolactone) with 91% selectivity to isoprene. In each case, by "total conversion" what is meant is the amount of mevalonolactone converted to products detectable by GC-FID within 4 minutes with a 45 degree column temperature, and explicitly does not include conversion to dehydrated mevalonolactone. It is expected that nearly 100% of mevalonolactone is consumed and converted to dehydrated mevalonolactone if it does not convert fully to other molecules.

Additional Experiments varied the residence time in the reactor, showing increased selectivity and conversion at low flow rates. At 250 C with 2.5 uL/min flow of 20 wt % mevalonolactone in water and carrier gas flow rate of 14.05 sccm showed isoprene peak area as 84% with methyl vinyl ketone as 14% of the peak area. Yield as compared to model stream suggests a total yield in excess of 48% isoprene for a minimum conversion of 56%. At an intermediate residence time with 7.01.4 sccm of carrier gas but other parameters left unchanged, the isoprene selectivity was 86% with methyl vinyl ketone as 11% of the peak area, and by the same estimation method a total conversion minimum of 67% for an overall yield of at least 59%.

Additional Experiments varied the temperature in the reactor, showing increased selectivity to isoprene at lower temperatures. At 300 C with 10 uL/min of 20% mevalonolactone in water and 28.13 sccm of nitrogen, the isoprene peak area is 72%, with estimated conversion of at least 66% for an overall yield of 47%.

Additional Experiments varied the concentration of mevalonolactone in water, using about 200 mg of Aerosil 380 silica catalyst. With 5 uL/min of 70% mevalonlactone in water and 14.05 sccm of nitrogen at 300 C, the product distribution shows 64% isoprene with 24% methyl vinyl ketone, 2% 2-methyl-1-butene, and 2% 2-methyl-1-propene. As temperature increases, the fraction of methyl vinyl ketone increases while isoprene decreases. At 350 C, isoprene is 36% of the peak area, methyl vinyl ketone is 33% of the peak area, 2-methyl-1-butene is 14% of the peak area, and 2-methyl-1-propene is 6% of the peak area. At 400 C, isoprene is 21% of the peak area, methyl vinyl ketone is 39% of the peak area, 2-methyl-1-butene is 33% of the peak area, and 2-methyl-1-propene is 6% of the peak area.

Additional Experiments removed the carrier gas and flowed 20% mevalonolactone at 2.5 uL/min into the reactor. At 250 C, the isoprene peak area was 91%, methyl vinyl ketone was 3%, and 2-methyl-1-propene was 4%. At even lower temperatures, we saw increased selectivity to isoprene. At 200 C, the isoprene peak area reached 96% with methyl vinyl ketone at 2.5%. At 150 C, the isoprene peak area reached 98.4% with methyl vinyl ketone at 1%.

Thus, by varying reactor temperature and residence time we can produce isoprene with exceptional selectivity, or switch to an intermediate condition to produce the desired product distribution of isoprene, methyl vinyl ketone, 1-methyl-2-butene, and 1-methyl-2-propene. This should not be taken as a limitation on the product distribution as our analytical tool only monitors low boiling point compounds quantitatively. Other products seen when analyzing the reactor products include but are not limited to 2-butene, 1,3-pentadiene, 2-methyl-1,3-butadiene, 2-butanone, 1,4-pentadiene-3-one, 1-pentene-3-one, 1-methyl-1,3-cyclohexadiene, 1-methyl-1,4-cyclohexadiene, toluene, 1-methylcyclohexa-2,4-diene, phenol, chlorobenzene, xylene, 4-penten-1-yl acetate, 1-(1,2-dimethyl-cyclopent-2-enyl)-ethanone, 4-acetyl-1-methylcyclohexene, and dehydrated mevalonolactone.

Example 37

Reaction of Mevalonolactone Over Palladium Supported on Silica

Using the same test reactor as in EXAMPLE 36, roughly 500 mg of SiliaCat Pd0 catalyst, palladium supported on silica, was tested. At 325 C with 10 uL/min of 20 wt % MVL in water and 28.13 sccm of nitrogen carrier gas, the isoprene peak area is roughly 68% with methyl vinyl ketone at 5%, 2-methyl-1-butene at 4%, 2-methyl-1-pentene at 6%, and 2-pentene at 15%.

Additional Experiments tested different temperature ranges and conditioning processes. When the catalyst is initially held at 275 C under 10 uL/min of 20 wt % MVL in water and 28.13 sccm of nitrogen, increasing temperature results in greater selectivity to isoprene, increasing from nearly zero selectivity to 75% selectivity at 375 C with high yield. However, when the catalyst is initially held at 400 C selectivity to isoprene increases as temperature goes down to 325 C, with 40% of peak area at 375 C, 55% at 350 C, and 68% at 325 C. This is indicative of palladium producing other isomers more preferentially, with palladium slowly being deactivated.

Additional Experiments tested different times on stream. As indicated in the temperature ramp direction test above, longer times on stream generally result in more palladium deactivation and higher isoprene selectivity versus other products. Other products include 2-pentene, 2-methyl-1-propene, 2-methyl-1-butene, methyl vinyl ketone, 1,3,5-tributyl-benzene, and other benzene derivatives.

Additional Experiments tested different residence times. With 5 uL/min of 20 wt % MVL in water plus 14.05 sccm of nitrogen at 325 C, isoprene area percentage is roughly 78%, with 11% for methyl vinyl ketone, 5% for 2-methyl-1-butene, and 6% for 2-methyl-1-propene. When the residence time is halved by increasing flow rate to 10 uL/min of liquid MVL solution and 28.13 sccm of nitrogen, isoprene peak area increases slightly to 82%, with 9% for methyl vinyl ketone, 3% for 2-methyl-1-butene, and 6% for 2-methyl-1-propene. When the residence time is reduced by a factor of 3, using a flow rate of 15 uL/min of MVL solution and 41.72 sccm of nitrogen, the isoprene peak area percentage decreases slightly to 81% with methyl vinyl ketone at 10%, 2-methyl-1-butene at 3%, and 2-methyl-1-propene at 7%. Based on this result, we estimate that the middle residence time is preferred for palladium supported on silica. With a roughly 1 gm/mL powder tap density, the 500 mg of catalyst has a volume of roughly 500 uL. At 325 C, 1 sccm of nitrogen is a real flow rate of about 2 mL/min. At 325 C, 1 uL/min of water flow is roughly 1 mL/min of real flow. Thus, with 10 uL/min of MVL solution in water and 28.13 sccm of nitrogen, we can estimate the real flow rate as 66.26 mL/min, for an estimated residence time of 0.45 seconds.

Additional Experiments tested varying MVL concentrations in water. All tests were done at 325 C and 40 sccm of nitrogen. Initially testing 10 uL/min of 100% MVL produced isoprene with 80% of the peak area, dropping to 58% after 86 minutes for an average of about 70%. Methyl vinyl ketone was present with about 16% of the peak area, 2-methyl-1-butene with 4%, and 2-methyl-1-propene with 6%. Decreasing 100% MVL flow rate to 5 uL/min resulted in an initial isoprene peak area of about 64%, dropping to 60% over 294 minutes. Methyl vinyl ketone was present with 21% of the peak area, 2-methyl-1-butene with 7%, and 2-methyl-1-propene with 7%. Using 70 wt % MVL in water, with flow rate of 5 uL/min isoprene peak area was slightly improved with about 70% of the peak area.

Example 38

Reaction of Mevalonolactone Over Alumina-Silica

Tests over alumina-silica catalyst Davicat SIAL 3113 were performed in the equipment described in EXAMPLE 36 in addition to the tests done using the reactor described in Example 11. In this follow up test, similar time on-stream behavior was seen as with EXAMPLE 37 wherein initial selectivity to isoprene was nearly zero, but after many hours on stream selectivity improved. Final performance of Davicat shows 73% of peak area as isoprene with 8% as methyl isopropyl ketone. This is most distinct from other tests in that methyl isopropyl ketone is present in substantial quantities whereas other catalysts and no catalyst tests produce almost no methyl isopropyl ketone and instead favor methyl vinyl ketone formation. In addition to the list of products shown in Example 11-14, we were able to identify several isomers of 1-ethyl-n-methyl Benzene, 1,3,5-trimethyl Benzene, 1-methyl-3-(1-methylethyl) Benzene, 1,4-diethyl-Benzene, 4-ethyl-1,2-dimethyl-Benzene, 1,2,4,5-tetramethyl-Benzene, 1,2,3,4-tetramethyl-Benzene, 1,2,4,5-tetramethyl-Benzene, and Diethyl Phthalate. Due to strong dependence on the time-on-stream for Davicat SIAL 3113 catalyst, numbers presented should be taken as general estimates only.

Additional Experiments varying the reactor temperature show that at 300 C, 30 uL/min of 20 wt % MVL in water with 28.13 sccm of nitrogen we see isoprene peak area start at 50% and increase to 83% over 300 minutes on stream with methyl isopropyl ketone decreasing from 20% to 4% in the same time period. At 350 C, 30 uL/min of 20 wt % MVL in water with 28.13 sccm of nitrogen isoprene peak area of about 73% while methyl isopropyl ketone was about 8% of peak area.

Additional Experiments varying pressure showed that higher pressures (500 PSI) result in decreased selectivity to isoprene in favor of Benzene derivatives.

Example 39

Reaction of Mevalonolactone Over Titania

Aeroxide Titania P25 was tested at temperatures ranging from 250 C to 350 C with 10 uL/min of 20 wt % MVL and 28.13 sccm of nitrogen with 500 mg of catalyst using the reactor described in EXAMPLE 36. At 350 C, isoprene represented 63% of the peak area with 13% as methyl vinyl ketone, 13% as 2-methyl-1-butene, and 8% as 2-methyl-1-propene. At 300 C, isoprene represented 68% of the peak area with 12% as methyl vinyl ketone, 8% as 2-methyl-1-butene, and 11% as 2-methyl-1-propene. At 250 C, isoprene represented 42% of the peak area with 49% as methyl vinyl ketone and 6% as 2-methyl-1-butene. Using the same conversion estimation method as described in EXAMPLE 36 using a model isoprene stream and ignoring conversion to aMVL, conversion at 250 C was at least 15% with 6% yield to isoprene. Conversion at 300 C was 44% with 30% minimum yield to isoprene. Conversion at 350 C was 55% with 35% minimum yield to isoprene.

Example 40

Reaction of Mevalonolactone without Catalyst

MVL solution was reacted with no catalyst through the reactor described in EXAMPLE 36, with roughly 3 mL of reactor internal volume heated but with no catalyst loaded at temperatures ranging from 300 C to 450 C. At all temperatures, 20 wt % MVL in water was flowed at 10 uL/min with 28.13 sccm of nitrogen carrier gas. At 300 C, isoprene represented 8% of overall peak area, 84% as methyl vinyl ketone, and 8% as 2-methyl-1-butene. Based on the model isoprene solution described in EXAMPLE 36, we estimate 11% overall conversion and 1% yield of isoprene. At 350 C, isoprene represented 12% of total peak area, with 71% as methyl vinyl ketone, 14% as 2-methyl-1-butene, and 3% as 2-methyl-1-propene. Estimated conversion is 30% with 3% isoprene yield. At 400 C, isoprene represented 14% of total peak area, with 54% as methyl vinyl ketone, 25% as 2-methyl-1-butene, and 5% as 2-methyl-1-propene. Estimated conversion is 44% with 6% yield of isoprene. At 450 C, isoprene represented 12% of total peak area, with 46% as methyl vinyl ketone, 32% as 2-methyl-1-butene, and 5% as 2-methyl-1-propene. Estimated conversion is 48% with 6% yield of isoprene. This result demonstrates clearly that without a catalyst isoprene is substantially less favorable as compared particularly to methyl vinyl ketone.

Example 41

Reaction of Mevalonolactone Over Nickel Metal Supported on Alumina

MVL was reacted over 66±5% Ni catalyst on silica alumina, catalog number 31276 from Alfa Aesar using the reactor described in EXAMPLE 36. At 300 C, 10 uL/min of 20 wt % MVL and 28.13 sccm of nitrogen resulted in only one visible peak on the in-line FID after vapor trap, presumed to be methane, carbon monoxide, or hydrogen. No isoprene, methyl vinyl ketone, methyl isopropyl ketone, or other known products were identified in the product stream. Decreasing reactor temperature to 250 C resulted in no significant change to the products visible.

Example 42

Reaction of Mevalonolactone with Ethanol Over Silica

Using the same test reactor as in EXAMPLE 36, 1.172 gm of Davisil Grade 62 Silica Gel was loaded and held at 300 C. In this example, ethanol is added as a co-reactant by mixing 3.638 gm of 20 wt % MVL in water with an additional 0.402 gm absolute ethanol in a syringe pump which was injected at 10 uL/min into the reactor alongside 2 sccm of nitrogen. After allowing the system to equilibrate for 30 minutes, the full product distribution was collected in either dichloromethane or 1-octanol to avoid missing product peaks due to overlap with solvent. In this example, the vapor trap and in-line GC-FID are bypassed to allow full product collection including heavy and high boiling point molecules. Mass spectra for the products in dichloromethane and 1-octanol were separately captured and analyzed. Some solvent contamination is expected, and as with all mass spectra identification is always somewhat ambiguous so this should not be taken as limiting the potential products produced using ethanol or any other coreactant.

The combined list of identified chemicals is
  Cyclobutanol
  4-Penten-2-ol, 3-methyl-
  Ethanol
  4-Penten-1-yl acetate
  1,3-Dioxolane, 2-heptyl-4-phenyl-
  Methyl vinyl ketone
  Ethyl acetate
  1,4-pentadien-3-one
  4-pentenoic acid ethyl ester
  Benzene, [(cyclohexyloxy)methyl]-
  Bicyclo[2.2.2]oct-7-en-2-one, 5-methylene-
  2,6-Octadien-1-ol, 2,7-dimethyl-
  P-Menth-1(7)-en-9-ol
  3-Cyclohexen-1-ol, 4-methyl-1-(1-methylethyl)-, acetate
  2,3-Epoxycarane, (E)-

Cyclohexanol, 1-methyl-4-(1-methylethenyl)-, acetate
Ethanol, 2-(3,3-dimethylcyclohexylidene)-, (Z)-
5-Caranol, trans, trans-(+)-
2-Furanone, 2,5-dihydro-3,5-dimethyl
3-Methylene-bicyclo[3.2.1]oct-6-en-8-ol
Benzeneethanol, .alpha., .alpha.-dimethyl-, acetate
2-Cyclohexen-1-one, 4,5-dimethyl-
(3 S,4R,5R,6R)-4,5-Bis(hydroxymethyl)-3,6-dimethylcyclohexene
4-Acetyl-1-methylcyclohexene
Cyclopentane, 1-acetyl-1,2-epoxy-
Ketone, 1,5-dimethylbicyclo[2.1.0]pent-5-yl methyl
Dehydromavalonic Lactone
Spiro[3.4]octan-5-one
1-Phthalanol, 1,3,3-trimethyl-
9-Octadecen-12-ynoic acid, methyl ester
2H-Pyran-2-one, 5,6-dihydro-4-(2,3-dimethyl-2-buten-2-yl)-
6-(p-Tolyl)-2-methyl-2-heptenol
4,4-Dimethylcyclohexadienone
Phenanthro[3,2-b]furan-7,11-dione, 1,2,3,4,8,9-hexahydro-4,4,8-trimethyl-, (+)-
1-Nonanol
Decanal
1-Decanol
Oxalic acid, isobutyl nonyl ester
Decanoic acid, methyl ester
Tetrahydropyran 12-tetradecyn-1-ol ether
Carbonic acid, octadecyl phenyl ester

The invention claimed is:

1. A process comprising reacting mevalonolactone, or a solution comprising mevalonolactone, at a temperature in the range of 100° C. to 500° C. and a pressure in the range of atmospheric pressure to less than 100 bar to yield a first product or first product mixture comprising at least one $C_5H_8$ compound,
wherein said reacting is performed in the absence of a catalyst.

2. The process of claim 1, wherein said at least one $C_5H_8$ compound comprises isoprene.

3. The process of claim 1, wherein said solution comprises a co-reactant.

4. The process of claim 3, wherein said co-reactant comprises water, an alkyl alcohol, an ether, an aromatic compound, an acid, an aldehyde, an ester, or a combination thereof.

5. The process of claim 1, wherein said first product or first product mixture further comprises at least one $C_{10}H_{16}$ compound.

6. The process of claim 1, further comprising reacting at least a portion of said first product or first product mixture in the presence of an acid catalyst to yield a second product or second product mixture, wherein said second product or second product mixture comprises at least one $C_{10}H_{16}$ compound.

7. A process comprising reacting mevalonolactone, or a solution comprising mevalonolactone, in the absence of a catalyst at a temperature greater than or equal to 100° C. and less than or equal to 500° C. and a pressure in the range of atmospheric pressure to less than 100 bar to yield a first product or first product mixture comprising isoprene.

8. The process of claim 7, wherein said first product further comprises anhydro-mevalonolactone, 1,3-Cyclohexadiene,1-methyl-4-(1-methylethyl), or a combination thereof.

9. The process of claim 7, wherein said solution comprises a co-reactant.

10. The process of claim 9, wherein said co-reactant comprises water, an alkyl alcohol, an ether, an aromatic compound, an acid, an aldehyde, an ester, or a combination thereof.

11. The process of claim 7, wherein said first product further comprises at least one $C_{10}H_{16}$ compound.

12. A process comprising:
(a) reacting mevalonolactone, or a solution comprising mevalonolactone, at a first temperature in the range of 100° C. to 500° C. and at a first pressure in the range of from atmospheric pressure to less than 100 bar to yield a first product or first product mixture,
wherein said reacting of step (a) is performed in the absence of a catalyst,
wherein said first product or first product mixture comprises isoprene; and
(b) reacting a first reagent with said first product or said first product mixture in the absence of a catalyst or in the presence of a solid catalyst at a second temperature greater than or equal to 50° C. and less than or equal to 200° C. to yield a second product or second product mixture,
wherein said solid catalyst comprises a mixed metal oxide, a supported transition metal, a supported noble metal, a supported transition metal, a supported noble metal, functionalized tetrafluoroethylene-fluoropolymer copolymers, calcium apatite, hydrotalcites, silica-alumina, silica, titania, sulfated zirconia, tungstated zirconia, alumina, or combinations thereof.

13. The process of claim 12, wherein said solution comprise a co-reactant.

14. The process of claim 13, wherein said co-reactant comprises water, an alkyl alcohol, an ether, an aromatic compound, an acid, an aldehyde, an ester, or a combination thereof.

15. The process of claim 12, wherein said first product further comprises anhydro-mevalonolactone, 1,3-Cyclohexadiene,1-methyl-4-(1-methylethyl), or a combination thereof.

16. The process of claim 12, wherein said first product further comprises at least one $C_{10}H_{16}$ compound.

* * * * *

SEQUENCE LISTING

<160> NUMBER OF SEQ ID NOS: 2

<210> SEQ ID NO 1
<211> LENGTH: 7935
<212> TYPE: DNA
<213> ORGANISM: Artificial Sequence
<220> FEATURE:
<223> OTHER INFORMATION: Synthetic plasmid pSE1

<400> SEQUENCE: 1

```
gtttgacagc ttatcatcga ctgcacggtg caccaatgct tctggcgtca ggcagccatc      60
ggaagctgtg gtatggctgt gcaggtcgta atcactgca taattcgtgt cgctcaaggc      120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgaaaac     420
agtagttatt attgatgcat tacgaacacc aattggaaaa tataaaggca gcttaagtca     480
agtaagtgcc gtagacttag aacacatgt tacaacacaa cttttaaaaa gacattccac     540
tatttctgaa gaaattgatc aagtaatctt tggaaatgtt ttacaagctg aaatggcca     600 aaatcccgca cgacaaatag caataaacag cggtttgtct catgaaattc cgcaatgac     660 ggttaatgag gtctgcggat caggaatgaa ggccgttatt ttggcgaaac aattgattca     720
attaggagaa gcggaagttt taattgctgg cgggattgag aatatgtccc aagcacctaa     780
attacaacgt tttaattacg aaacagaaag ctacgatgcg ccttttttcta gtatgatgta     840 tgatggatta acggatgcct ttagtggtca ggcaatgggc ttaactgctg aaaatgtggc     900
cgaaaagtat catgtaacta gagaagagca agatcaattt tctgtacatt cacaattaaa     960
agcagctcaa gcacaagcag aagggatatt cgctgacgaa atagcccat tagaagtatc     1020 aggaacgctt gtggagaaag atgaagggat tcgccctaat tcgagcgttg agaagctagg    1080
aacgcttaaa acagttttta agaagacgg tactgtaaca gcagggaatg catcaaccat    1140
taatgatggg gcttctgctt tgattattgc ttcacaagaa tatgccgaag cacacggtct    1200
tccttattta gctattattc gagacagtgt ggaagtcggt attgatccag cctatatggg    1260
aatttcgccg attaaagcca ttcaaaaact gttagcgcgc aatcaactta ctacggaaga    1320
aattgatctg tatgaaatca acgaagcatt tgcagcaact tcaatcgtgg tccaaagaga    1380
actggctttt ccagaggaaa aggtcaacat ttatggtggc ggtatttcat taggtcatgc    1440
```

-continued

```
gattggtgcc acaggtgctc gtttattaac gagtttaagt tatcaattaa atcaaaaaga    1500
aaagaaatat ggagtggctt ctttatgtat cggcggtggc ttaggactcg ctatgctact    1560
agagagacct cagcaaaaaa aaaacagccg attttatcaa atgagtcctg aggaacgcct    1620
ggcttctctt cttaatgaag gccagatttc tgctgataca aaaaaagaat ttgaaaatac    1680
ggctttatct tcgcagattg ccaatcatat gattgaaaat caaatcagtg aaacagaagt    1740
gccgatgggc gttggcttac atttaacagt ggacgaaact gattatttgg taccaatggc    1800
gacagaagag ccctcagtta ttgcggcttt gagtaatggt gcaaaaatag cacaaggatt    1860
taaaacagtg aatcaacaac gcttaatgcg tggacaaatc gttttttacg atgttgcaga    1920
tcccgagtca ttgattgata aactacaagt aagagaagcg gaagtttttc aacaagcaga    1980
gttaagttat ccatctatcg ttaaacgggg cggcggctta agagatttgc aatatcgtac    2040
ttttgatgaa tcatttgtat ctgtcgactt tttagtagat gttaaggatg caatgggggc    2100
aaatatcgtt aacgctatgt tggaaggtgt ggccgagttg ttccgtgaat ggtttgcgga    2160
gcaaaagatt ttattcagta ttttaagtaa ttatgccacg gagtcggttg ttacgatgaa    2220
aacggctatt ccagttttcac gtttaagtaa ggggagcaat ggccgggaaa ttgctgaaaa    2280
aattgtttta gcttcacgct atgcttcatt agatccttat cgggcagtca cgcataacaa    2340
aggaatcatg aatggcattg aagctgtagt tttagctaca ggaaatgata cacgcgctgt    2400
tagcgcttct tgtcatgctt ttgcggtgaa ggaaggtcgc taccaaggct tgactagttg    2460
gacgctggat ggcgaacaac taattggtga aatttcagtt ccgcttgctt tagccacggt    2520
tggcggtgcc acaaaagtct tacctaaatc tcaagcagct gctgatttgt tagcagtgac    2580
ggatgcaaaa gaactaagtc gagtagtagc ggctgttggt ttggcacaaa atttagcggc    2640
gttacgggcc ttagtctctg aaggaattca aaaaggacac atggcctcta agcacgttc    2700
tttagcgatg acggtcggag ctactggtaa agaagttgag gcagtcgctc aacaattaaa    2760
acgtcaaaaa acgatgaacc aagaccgagc catggctatt ttaaatgatt taagaaaaca    2820
ataagatcta aggagttaaa gaaatgacaa ttgggattga taaaattagt ttttttgtgc    2880
ccccttatta tattgatatg acggcactgg ctgaagccag aaatgtagac cctggaaaat    2940
ttcatattgg tattgggcaa gaccaaatgg cggtgaaccc aatcagccaa gatattgtga    3000
catttgcagc caatgccgca gaagcgatct tgaccaaaga agataaagag gccattgata    3060
tggtgattgt cgggactgag tccagtatcg atgagtcaaa agcggccgca gttgtcttac    3120
atcgtttaat ggggattcaa cctttcgctc gctctttcga aatcaaggaa ggttgttacg    3180
gagcaacagc aggcttacag ttagctaaga atcacgtagc cttacatcca gataaaaaag    3240
tcttggtcgt agcggcagat attgcaaaat atggcttaaa ttctggcggt gagcctacac    3300
aaggagctgg ggcggttgca atgttagttg ctagtgaacc gcgcatttg gctttaaaag    3360
aggataatgt gatgctgacg caagatatct atgacttttg gcgtccaaca ggccaccccgt    3420
atcctatggt cgatggtcct ttgtcaaacg aaacctacat ccaatctttt gcccaagtct    3480
gggatgaaca taaaaaacga accggtcttg attttgcaga ttatgatgct ttagcgttcc    3540
atattcctta cacaaaaatg ggcaaaaaag cctattagc aaaaatctcc gaccaaactg    3600
aagcagaaca ggaacgaatt ttagcccgtt atgaagaaag tatcgtctat agtcgtcgcg    3660
taggaaactt gtatacgggt tcactttatc tgggactcat ttcccttta gaaaatgcaa    3720
cgactttaac cgcaggcaat caaattggtt tattcagtta tggttctggt gctgtcgctg    3780
aattttttcac tggtgaatta gtagctggtt atcaaaatca tttacaaaaa gaaactcatt    3840
```

```
tagcactgct ggataatcgg acagaacttt ctatcgctga atatgaagcc atgtttgcag    3900
aaactttaga cacagacatt gatcaaacgt tagaagatga attaaaatat agtatttctg    3960
ctattaataa taccgttcgt tcttatcgaa actaatctag aacaaaaact catctcagaa    4020
gaggatctga atagcgccgt cgaccatcat catcatcatc attgagttta aacggtctcc    4080
agcttggctg ttttggcgga tgagagaaga ttttcagcct gatacagatt aaatcagaac    4140
gcagaagcgg tctgataaaa cagaatttgc ctggcggcag tagcgcggtg gtcccacctg    4200
accccatgcc gaactcagaa gtgaaacgcc gtagcgccga tggtagtgtg gggtctcccc    4260
atgcgagagt agggaactgc caggcatcaa ataaaacgaa aggctcagtc gaaagactgg    4320
gcctttcgtt ttatctgttg tttgtcggtg aacgctctcc tgagtaggac aaatccgccg    4380
ggagcggatt tgaacgttgc gaagcaacgg cccggagggt ggcgggcagg acgcccgcca    4440
taaactgcca ggcatcaaat taagcagaag gccatcctga cggatggcct ttttgcgttt    4500
ctacaaactc ttttttgttta tttttctaaa tacattcaaa tatgtatccg ctcatgagac    4560
aataaccctg ataaatgctt caataatatt gaaaaaggaa gagtatgagt attcaacatt    4620
tccgtgtcgc ccttattccc ttttttgcgg cattttgcct tcctgttttt gctcacccag    4680
aaacgctggt gaaagtaaaa gatgctgaag atcagttggg tgcacgagtg ggttacatcg    4740
aactggatct caacagcggt aagatccttg agagttttcg ccccgaagaa cgttttccaa    4800
tgatgagcac ttttaaagtt ctgctatgtg gcgcggtatt atcccgtgtt gacgccgggc    4860
aagagcaact cggtcgccgc atacactatt ctcagaatga cttggttgag tactcaccag    4920
tcacagaaaa gcatcttacg gatggcatga cagtaagaga attatgcagt gctgccataa    4980
ccatgagtga taacactgcg gccaacttac ttctgacaac gatcggagga ccgaaggagc    5040
taaccgcttt tttgcacaac atgggggatc atgtaactcg ccttgatcgt tgggaaccgg    5100
agctgaatga agccatacca aacgacgagc gtgacaccac gatgcctgta gcaatggcaa    5160
caacgttgcg caaactatta actggcgaac tacttactct agcttcccgg caacaattaa    5220
tagactggat ggaggcggat aaagttgcag gaccacttct gcgctcggcc cttccggctg    5280
gctggtttat tgctgataaa tctggagccg gtgagcgtgg gtctcgcggt atcattgcag    5340
cactggggcc agatggtaag ccctcccgta tcgtagttat ctacacgacg gggagtcagg    5400
caactatgga tgaacgaaat agacagatcg ctgagatagg tgcctcactg attaagcatt    5460
ggtaactgtc agaccaagtt tactcatata ctttagattg atttaaaaa cttcattttt    5520 aatttaaaag gatctaggtg aagatccttt ttgataatct catgaccaaa atcccttaac    5580
gtgagttttc gttccactga gcgtcagacc ccgtagaaaa gatcaaagga tcttcttgag    5640
atcctttttt tctgcgcgta atctgctgct tgcaaacaaa aaaaccaccg ctaccagcgg    5700
tggtttgttt gccggatcaa gagctaccaa ctctttttcc gaaggtaact ggcttcagca    5760
gagcgcagat accaaatact gtccttctag tgtagccgta gttaggccac cacttcaaga    5820
actctgtagc accgcctaca tacctcgctc tgctaatcct gttaccagtg gctgctgcca    5880
gtggcgataa gtcgtgtctt accgggttgg actcaagacg atagttaccg gataaggcgc    5940
agcggtcggg ctgaacgggg ggttcgtgca cacagcccag cttggagcga acgacctaca    6000
ccgaactgag atacctacag cgtgagctat gagaaagcgc cacgcttccc gaagggagaa    6060
aggcggacag gtatccggta agcggcaggg tcggaacagg agagcgcacg agggagcttc    6120 caggggggaaa cgcctggtat ctttatagtc ctgtcgggtt tcgccacctc tgacttgagc    6180
```

| gtcgattttt gtgatgctcg tcagggggc ggagcctatg gaaaaacgcc agcaacgcgg | 6240 |
| ccttttacg gttcctggcc ttttgctggc cttttgctca catgttcttt cctgcgttat | 6300 |
| cccctgattc tgtggataac cgtattaccg cctttgagtg agctgatacc gctcgccgca | 6360 |
| gccgaacgac cgagcgcagc gagtcagtga gcgaggaagc ggaagagcgc ctgatgcggt | 6420 |
| attttctcct tacgcatctg tgcggtattt cacaccgcat atggtgcact ctcagtacaa | 6480 |
| tctgctctga tgccgcatag ttaagccagt atacactccg ctatcgctac gtgactgggt | 6540 |
| catggctgcg ccccgacacc cgccaacacc cgctgacgcg ccctgacggg cttgtctgct | 6600 |
| cccggcatcc gcttacagac aagctgtgac cgtctccggg agctgcatgt gtcagaggtt | 6660 |
| ttcaccgtca tcaccgaaac gcgcgaggca gcagatcaat tcgcgcgcga aggcgaagcg | 6720 |
| gcatgcattt acgttgacac catcgaatgg tgcaaaacct ttcgcggtat ggcatgatag | 6780 |
| cgcccggaag agagtcaatt cagggtggtg aatgtgaaac cagtaacgtt atacgatgtc | 6840 |
| gcagagtatg ccggtgtctc ttatcagacc gtttcccgcg tggtgaacca ggccagccac | 6900 |
| gtttctgcga aaacgcggga aaagtggaa gcggcgatgg cggagctgaa ttacattccc | 6960 |
| aaccgcgtgg cacaacaact ggcgggcaaa cagtcgttgc tgattggcgt tgccacctcc | 7020 |
| agtctggccc tgcacgcgcc gtcgcaaatt gtcgcggcga ttaaatctcg cgccgatcaa | 7080 |
| ctgggtgcca gcgtggtggt gtcgatggta gaacgaagcg gcgtcgaagc ctgtaaagcg | 7140 |
| gcggtgcaca atcttctcgc gcaacgcgtc agtgggctga tcattaacta tccgctggat | 7200 |
| gaccaggatg ccattgctgt ggaagctgcc tgcactaatg ttccggcgtt atttcttgat | 7260 |
| gtctctgacc agacacccat caacagtatt attttctccc atgaagacgg tacgcgactg | 7320 |
| ggcgtggagc atctggtcgc attgggtcac cagcaaatcg cgctgttagc gggcccatta | 7380 |
| agttctgtct cggcgcgtct gcgtctggct ggctggcata atatctcac tcgcaatcaa | 7440 |
| attcagccga tagcggaacg ggaaggcgac tggagtgcca tgtccggttt tcaacaaacc | 7500 |
| atgcaaatgc tgaatgaggg catcgttccc actgcgatgc tggttgccaa cgatcagatg | 7560 |
| gcgctgggcg caatgcgcgc cattaccgag tccgggctgc gcgttggtgc ggatatctcg | 7620 |
| gtagtgggat acgacgatac cgaagacagc tcatgtttata tcccgccgtc aaccaccatc | 7680 |
| aaacaggatt ttcgcctgct ggggcaaacc agcgtggacc gcttgctgca actctctcag | 7740 |
| ggccaggcgg tgaagggcaa tcagctgttg cccgtctcac tggtgaaaag aaaaaccacc | 7800 |
| ctggcgccca atacgcaaac cgcctctccc cgcgcgttgg ccgattcatt aatgcagctg | 7860 |
| gcacgacagg tttcccgact ggaaagcggg cagtgagcgc aacgcaatta atgtgagtta | 7920 |
| gcgcgaattg atctg | 7935 |

<210> SEQ ID NO 2
<211> LENGTH: 10857
<212> TYPE: DNA
<213> ORGANISM: Artificial Sequence
<220> FEATURE:
<223> OTHER INFORMATION: Synthetic plasmid pVS19

<400> SEQUENCE: 2

| gacgaaaggg cctcgtgata cgcctatttt tataggttaa tgtcatgata ataatggttt | 60 |
| cttagatgat ccaatatcaa aggaaatgat agcattgaag gatgagacta atccaattga | 120 |
| ggagtggcag catatagaac agctaaaggg tagtgctgaa ggaagcatac gatacccgc | 180 |
| atggaatggg ataatatcac aggaggtact agactacctt tcatcctaca taatagacg | 240 |
| catataagta cgcatttaag cataaacacg cactatgccg ttcttctcat gtatatatat | 300 |

```
atacaggcaa cacgcagata taggtgcgac gtgaacagtg agctgtatgt gcgcagctcg    360
cgttgcattt tcggaagcgc tcgttttcgg aaacgctttg aagttcctat tccgaagttc    420
ctattctcta gctagaaagt ataggaactt cagagcgctt ttgaaaacca aaagcgctct    480
gaagacgcac tttcaaaaaa ccaaaaacgc accggactgt aacgagctac taaaatattg    540
cgaataccgc ttccacaaac attgctcaaa agtatctctt tgctatatat ctctgtgcta    600
tatccctata taacctaccc atccaccttt cgctccttga acttgcatct aaactcgacc    660
tctacatttt ttatgtttat ctctagtatt actcttagga caaaaaatt gtagtaagaa     720 ctattcatag agtgaatcga aaacaatacg aaaatgtaaa catttcctat acgtagtata    780
tagagacaaa atagaagaaa ccgttcataa ttttctgacc aatgaagaat catcaacgct    840
atcactttct gttcacaaag tatgcgcaat ccacatcggt atagaatata atcggggatg    900
cctttatctt gaaaaatgc acccgcagct cgctagtaa tcagtaaacg cgggaagtgg      960
agtcaggctt tttttatgga agagaaaata gacaccaaag tagccttctt ctaaccttaa   1020
cggacctaca gtgcaaaaag ttatcaagag actgcattat agagcgcaca aaggagaaaa   1080
aaagtaatct aagatgcttt gttagaaaaa tagcgctctc gggatgcatt tttgtagaac   1140
aaaaaagaag tatagattct ttgttggtaa aatagcgctc tcgcgttgca tttctgttct   1200
gtaaaaatgc agctcagatt cttttgtttga aaaattagcg ctctcgcgtt gcatttttgt  1260
tttacaaaaa tgaagcacag attcttcgtt ggtaaaatag cgctttcgcg ttgcatttct   1320
gttctgtaaa aatgcagctc agattctttg tttgaaaaat tagcgctctc gcgttgcatt   1380
tttgttctac aaaatgaagc acagatgctt cgttcaggtg cacttttcg gggaaatgtg    1440 cgcggaaccc ctatttgttt attttctaa atacattcaa atatgtatcc gctcatgaga     1500
caataaccct gataaatgct tcaataatat tgaaaaagga agagtatgag tattcaacat    1560
ttccgtgtcg ccccttattcc cttttttgcg catttttgcc ttcctgtttt tgctcaccca   1620
gaaacgctgg tgaaagtaaa agatgctgaa gatcagttgg gtgcacgagt gggttacatc    1680
gaactggatc tcaacagcgg taagatcctt gagagttttc gccccgaaga acgttttcca    1740
atgatgagca cttttaaagt tctgctatgt ggcgcggtat tatcccgtat tgacgccggg    1800
caagagcaac tcggtcgccg catacactat tctcagaatg acttggttga gtactcacca    1860
gtcacagaaa agcatcttac ggatggcatg acagtaagag aattatgcag tgctgccata    1920
accatgagtg ataacactgc ggccaactta cttctgacaa cgatcggagg accgaaggag    1980
ctaaccgctt ttttgcacaa catgggggat catgtaactc gccttgatcg ttgggaaccg    2040
gagctgaatg aagccatacc aaacgacgag cgtgacacca cgatgcctgt agcaatggca    2100
acaacgttgc gcaaactatt aactggcgaa ctacttactc tagcttcccg gcaacaatta    2160
atagactgga tggaggcgga taaagttgca ggaccacttc tgcgctcggc ccttccggct    2220
ggctggttta ttgctgataa atctggagcc ggtgagcgtg ggtctcgcgg tatcattgca    2280 gcactgggc cagatggtaa gccctcccgt atcgtagtta tctacacgac ggggagtcag    2340
gcaactatgg atgaacgaaa tagacagatc gctgagatag gtgcctcact gattaagcat    2400
tggtaactgt cagaccaagt ttactcatat atactttaga ttgatttaaa acttcatttt   2460
taatttaaaa ggatctaggt gaagatcctt tttgataatc tcatgaccaa aatcccttaa    2520
cgtgagtttt cgttccactg agcgtcagac cccgtagaaa agatcaaagg atcttcttga    2580 gatcctttttt ttctgcgcgt aatctgctgc ttgcaaacaa aaaaaccacc gctaccagcg   2640
```

```
gtggtttgtt tgccggatca agagctacca actcttttc  cgaaggtaac tggcttcagc   2700
agagcgcaga taccaaatac tgttcttcta gtgtagccgt agttaggcca ccacttcaag   2760
aactctgtag caccgcctac atacctcgct ctgctaatcc tgttaccagt ggctgctgcc   2820
agtggcgata agtcgtgtct taccggggttg gactcaagac gatagttacc ggataaggcg   2880
cagcggtcgg gctgaacggg gggttcgtgc acacagccca gcttggagcg aacgacctac   2940
accgaactga gatacctaca gcgtgagcta tgagaaagcg ccacgcttcc cgaagggaga   3000
aaggcggaca ggtatccggt aagcggcagg gtcggaacag gagagcgcac gagggagctt   3060
ccagggggaa acgcctggta tctttatagt cctgtcgggt ttcgccacct ctgacttgag   3120
cgtcgatttt tgtgatgctc gtcagggggg cggagcctat ggaaaaacgc cagcaacgcg   3180
gcctttttac ggttcctggc cttttgctgg ccttttgctc acatgttctt tcctgcgtta   3240
tcccctgatt ctgtggataa ccgtattacc gcctttgagt gagctgatac cgctcgccgc   3300
agccgaacga ccgagcgcag cgagtcagtg agcgaggaag cggaagagcg cccaatacgc   3360
aaaccgcctc tccccgcgcg ttggccgatt cattaatgca gctggcacga caggtttccc   3420
gactggaaag cgggcagtga gcgcaacgca attaatgtga gttagctcac tcattaggca   3480
ccccaggctt tacactttat gcttccggct cgtatgttgt gtggaattgt gagcggataa   3540
caatttcaca caggaaacag ctatgaccat gattacgcca agcgcgcaat taaccctcac   3600
taaagggaac aaaagctgga gctcaccggt atacccggga aacagctgag tttatcatta   3660
tcaatactcg ccatttcaaa gaatacgtaa ataattaata gtagtgattt tcctaacttt   3720
atttagtcaa aaaattagcc ttttaattct gctgtaaccc gtacatgccc aaaatagggg   3780
gcgggttaca cagaatatat aacatcgtag gtgtctgggt gaacagttta ttcctggcat   3840
ccactaaata taatggagcc cgcttttaa  gctggcatcc agaaaaaaaa agaatcccag   3900
caccaaaata ttgttttctt caccaaccat cagttcatag gtccattctc ttagcgcaac   3960
tacagagaac aggggcacaa acaggcaaaa aacgggcaca acctcaatgg agtgatgcaa   4020
cctgcctgga gtaaatgatg acacaaggca attgacccac gcatgtatct atctcatttt   4080
cttcaccctt ctattacctt ctgctctctc tgatttggaa aaagctgaaa aaaaaggttg   4140
aaaccagttc cctgaaatta ttcccctact tgactaataa gtatataaag acggtaggta   4200
ttgattgtaa ttctgtaaat ctatttctta aacttcttaa attctacttt tatagttagt   4260
ctttttttta gttttaaaac accagaactt agtttcgacg gattggcggc cgctaaaatc   4320
atggctagca agacggtcgt cattattgac gcacttcgta ctcctattgg taaatacaaa   4380
ggttctttgt ctcaagtttc cgctgttgat ttgggtactc atgtcaccac acagttgctt   4440
aaacgtcact ctacaatttc tgaggaaatt gaccaggtta ttttggtaa  cgttttgcaa   4500 gccggcaatg gtcaaaaccc agctcgtcaa attgccatta atagtggact ttctcatgaa   4560
attccagcta tgactgtgaa cgaagtttgc ggatctggca tgaaagcagt tattttggca   4620
aaacaactta tccaacttgg agaagctgag gtgttgatcg caggtggcat cgaaaatatg   4680
tctcaggctc caaaattgca acgttttaac tacgaaacgg agtcttacga tgccccattt   4740
agttctatga tgtacgacgg tttgacagat gcatttttcg gtcaagcaat gggttttgacc  4800 gccgaaaatg tcgctgaaaa gtatcatgtg acgcgtgaag aacaagacca attttccgtc   4860
catagtcaac ttaaagctgc ccaagctcag gcagaaggta tttttgccga tgaaatcgcc   4920
cctcttgagg tttccggtac acttgttgag aaagatgaag gtattcgtcc taatagttcc   4980
gtcgaaaagt tgggaacact taagactgtc ttcaaggagg atggaacggt gacagcaggt   5040
```

```
aacgcttcta caattaatga tggtgcatct gctttgatta ttgcctccca agaatatgct    5100
gaagcacatg gtttgccata tttggccatc atccgtgact ccgttgaggt cggcattgat    5160
cctgcctata tgggcatttc cccaatcaag gcaattcaaa agttgttggc tcgtaatcaa    5220
cttacaactg aagagattga tctttatgag atcaatgagg cctttgctgc cacttccatt    5280
gttgttcagc gtgaattggc tttgcctgaa gaaaagtga acatttacgg aggtggaatc     5340
tctttgggac atgcaatcgg cgcaaccggc gcacgtcttt tgacctctct ttcttatcag    5400
ttgaatcaaa aggaaaaaaa gtacggtgtg ctagtttgt gtattggagg tggcttggga     5460
ttggcaatgt tgttggagcg tcctcaacaa aagaaaaact cccgtttcta tcagatgagt    5520
cctgaagaac gtcttgcttc cttgttgaat gagggccaga ttagtgctga tacgaagaaa    5580
gagttcgaaa acaccgcact ttcttctcag attgctaacc acatgattga aaatcagatt    5640
tccgaaactg aagttccaat gggagtggga ttgcatttga ctgttgacga gactgattat    5700
ttggtgccaa tggctactga agaaccatct gtgatcgccg ccctttctaa cggtgcaaag    5760
attgctcagg gatttaaaac tgtcaatcag caacgtctta tgcgtggaca gatcgttttc    5820
tacgatgtcg cagaccctga gtcccttatt gataaacttc aagttcgtga agctgaagtc    5880
ttccagcaag cagaacttag ttatccttct atcgtcaaac gtggtggcgg cttgcgtgat    5940
ttgcaatatc gtactttcga cgagagtttt gttagtgtgg atttttttggt tgatgtgaag    6000 gacgcaatgg gtgcaaatat cgttaacgca atgttggaag gcgttgctga attgtttcgt    6060
gaatggttcg ccgaacaaaa gattttgttc tccattttgt ccaattacgc tacagaatct    6120
gttgtcacaa tgaagactgc catccctgtg tctcgtttgt ctaaaggtag taacggtcgt    6180
gaaattgcag aaaaaatcgt gttggcaagt cgttatgcta gtcttgatcc atatcgtgcc    6240
gttacgcaca ataaaggtat catgaacggt atcgaagctg tggtcttggc caccggcaat    6300
gatacacgtg ctgtcagtgc aagttgtcat gcatttgcag ttaaagaagg tcgttaccaa    6360
ggattgactt cctggacttt ggatggtgag caacttattg gcgaaatttc tgttccattg    6420
gctcttgcta ccgttggtgg tgccacaaaa gttcttccaa agtctcaagc tgccgctgac    6480
ttgttggctg ttaccgacgc taaagagctt agtcgtgttg ttgcagctgt cggtttggct    6540
caaaatttgg ctgcattgcg tgccttggtt agtgaaggta tccaaaaagg tcacatggcc    6600
ttgcaagctc gttccttggc tatgaccgtt ggagctacag gtaaggaagt ggaagctgtt    6660
gcacaacagt tgaagcgtca aaaaactatg aatcaagatc gtgctatggc cattttgaat    6720
gatttgcgta acaactcga gtaatgatca gcgaatttct tatgatttat gatttttatt     6780
attaaataag ttataaaaaa aataagtgta tacaaatttt aaagtgactc ttaggtttta    6840
aaacgaaaat tcttattctt gagtaactct ttcctgtagg tcaggttgct ttctcaggta    6900
tagcatgagg tcgctcttat cgccgggaaa cagctgatag cttcaaaatg tttctactcc    6960
ttttttactc ttccagattt tctcggactc cgcgcatcgc cgtaccactt caaaacaccc    7020
aagcacagca tactaaattt cccctctttc ttcctctagg gtgtcgttaa ttacccgtac    7080
taaaggtttg gaaaagaaaa aagagaccgc ctcgtttctt tttcttcgtc gaaaaaggca    7140
ataaaaattt ttatcacgtt tcttttttctt gaaaattttt tttttgattt ttttctcttt    7200
cgatgacctc ccattgatat ttaagttaat aaacggtctt caatttctca gtttcagtt     7260 tcattttttct tgttctatta caactttttt tacttcttgc tcattagaaa gaaagcatag    7320
caatctaatc taagttttgg cggccgctaa aatcatggct agcaccatcg gcatcgacaa    7380
```

-continued

```
gatttctttc ttcgttccac catattacat tgacatgacg gctttggctg aagcccgtaa    7440
cgttgatcct ggtaaattcc atattggaat cggccaggac caaatggctg tgaatccaat    7500
cagtcaagat attgtcactt tcgcagcaaa cgccgcagaa gccattttga ctaaagagga    7560
taaggaagct attgacatgg ttattgtcgg cactgaaagt tccattgatg aatctaaggc    7620
agctgctgtc gttcttcatc gtcttatggg tattcaacca tttgcacgta gttttgaaat    7680
taaagaggga tgttatggag caaccgcagg cttgcagttg caaaaaatc atgtggcttt     7740 gcatccagat aaaaaggttt tggttgttgc agccgatatt gctaagtacg gattgaatag    7800
tggtggtgag ccaacgcaag gtgcaggagc tgttgcaatg ttggttgcta gtgaacctcg    7860
tatccttgcc ttgaaggaag ataacgtcat gttgacccag gatatttatg attttttggcg   7920 tccaacaggc catccttacc ctatggtcga tggtcctctt agtaatgaaa catacattca    7980
atcttttgcc caagtctggg atgaacacaa aaagcgtaca ggtcttgatt ttgccgatta    8040
tgatgccctt gctttccaca ttccttacac taaaatgggt aagaaagcat tgttggctaa    8100
aatttctgac caaactgaag ccgaacagga acgtatcttg gctcgttatg aagaatctat    8160
cgtgtactct cgtcgtgtgg gtaacccttta tacaggttct ctttatcttg gattgatttc    8220
cttgcttgag aatgctacta ctttgacggc tggaaatcag atcggtttgt ttcctatgg     8280 ttctggcgct gttgctgagt ttttttacagg tgaattggtt gcaggttacc aaaatcactt    8340
gcaaaaagag acacatcttg ctttgttgga taatcgtacc gaattgtcta tcgctgaata    8400
tgaagcaatg ttcgctgaga ctttggacac agatattgac caaacccttg aggacgaatt    8460
gaaatattcc atctccgcca ttaacaatac tgtgcgttcc taccgtaacc tcgagtaatg    8520
atcatctctg cttttgtgcg cgtatgttta tgtatgtacc tctctctcta tttctatttt    8580
taaaccaccc tctcaataaa ataaaaataa taaagtatt ttaaggaaaa gacgtgttta     8640
agcactgact ttatctactt tttgtacgtt tcattgata taatgtgttt tgtctctccc     8700
ttttctacga aaatttcaaa aattgaccaa aaaaggaat atatacga aaaactatta      8760 tatttatata tcatagtgtt gataaaaat gtttatccat tggaccgtgt atcatattta     8820
tcgccggcga ataaattaag gcgcgccaac atatccggag gtacccaatt cgccctatag    8880
tgagtcgtat tacgcgcgct cactggccgt cgttttacaa cgtcgtgact gggaaaaccc    8940
tggcgttacc caacttaatc gccttgcagc acatccccct ttcgccagct ggcgtaatag    9000
cgaagaggcc cgcaccgatc gcccttccca acagttgcgc agcctgaatg gcgaatggac    9060
gcgccctgta gcggcgcatt aagcgcggcg ggtgtggtgg ttacgcgcag cgtgaccgct    9120
acacttgcca gcgccctagc gcccgctcct ttcgctttct tcccttcctt tctcgccacg    9180
ttcgccggct ttccccgtca gctctaaatc gggggctcc ctttagggtt ccgatttagt     9240
gctttacggc acctcgaccc caaaaaactt gattagggtg atggttcacg tagtgggcca    9300
tcgccctgat agacggtttt tcgccctttg acgttggagt ccacgttctt taatagtgga    9360
ctcttgttcc aaactggaac aacactcaac cctatctcgg tctattcttt tgatttataa    9420
gggattttgc cgatttcggc ctattggtta aaaatgagc tgatttaaca aaatttaac      9480 gcgaatttta acaaaatatt aacgcttaca atttcctgat gcggtatttt ctccttacgc    9540
atctgtgcgg tatttcacac cgcatagggt aataactgat ataattaaat tgaagctcta    9600
atttgtgagt ttagtataca tgcatttact tataatacag ttttttagtt ttgctggccg    9660
catcttctca aatatgcttc ccagcctgct tttctgtaac gttcaccctc taccttagca    9720
tcccttccct ttgcaaatag tcctcttcca acaataataa tgtcagatcc tgtagagacc    9780
```

```
acatcatcca cggttctata ctgttgaccc aatgcgtctc ccttgtcatc taaacccaca    9840
ccgggtgtca taatcaacca atcgtaacct tcatctcttc cacccatgtc tctttgagca    9900
ataaagccga taacaaaatc tttgtcgctc ttcgcaatgt caacagtacc cttagtatat    9960
tctccagtag atagggagcc cttgcatgac aattctgcta acatcaaaag gcctctaggt   10020
tcctttgtta cttcttctgc cgcctgcttc aaaccgctaa caatacctgg tcccaccaca   10080
ccgtgtgcat tcgtaatgtc tgcccattct gctattctgt atacacccgc agagtactgc   10140
aatttgactg tattaccaat gtcagcaaat tttctgtctt cgaagagtaa aaaattgtac   10200
ttggcggata atgcctttag cggcttaact gtgccctcca tggaaaaatc agtcaagata   10260
tccacatgtg tttttagtaa acaaattttg ggacctaatg cttcaactaa ctccagtaat   10320
tccttggtgg tacgaacatc caatgaagca cacaagtttg tttgcttttc gtgcatgata   10380
ttaaatagct tggcagcaac aggactagga tgagtagcag cacgttcctt atatgtagct   10440
ttcgacatga tttatcttcg tttcctgcat gtttttgttc tgtgcagttg ggttaagaat   10500
actgggcaat ttcatgtttc ttcaacacta catatgcgta tatataccaa tctaagtctg   10560
tgctccttcc ttcgttcttc cttctgttcg gagattaccg aatcaaaaaa atttcaagga   10620
aaccgaaatc aaaaaaaaga ataaaaaaaa aatgatgaat tgaaaggtg gtatggtgca    10680 ctctcagtac aatctgctct gatgccgcat agttaagcca gccccgacac ccgccaacac   10740
ccgctgacgc gccctgacgg gcttgtctgc tcccggcatc cgcttacaga caagctgtga   10800
ccgtctccgg gagctgcatg tgtcagaggt tttcaccgtc atcaccgaaa cgcgcga      10857
```